(12) United States Patent
Lazarus et al.

(10) Patent No.: US 8,030,341 B2
(45) Date of Patent: Oct. 4, 2011

(54) DMT-DERIVATIVE COMPOUNDS AND RELATED COMPOSITIONS AND METHODS OF USE

(75) Inventors: Lawrence H. Lazarus, Durham, NC (US); Yoshio Okada, Akashi (JP); Tingyou Li, Akashi (JP)

(73) Assignees: The United States of America as represented by the Secretary of the Department of Health and Human Services, Washington, DC (US); Kobe Gakuin University, Kobe (JP)

( * ) Notice: Subject to any disclaimer, the term of this patent is extended or adjusted under 35 U.S.C. 154(b) by 823 days.

(21) Appl. No.: 12/065,121

(22) PCT Filed: Aug. 30, 2006

(86) PCT No.: PCT/US2006/033560
§ 371 (c)(1),
(2), (4) Date: Apr. 2, 2008

(87) PCT Pub. No.: WO2007/027628
PCT Pub. Date: Mar. 8, 2007

(65) Prior Publication Data
US 2008/0269143 A1 Oct. 30, 2008

Related U.S. Application Data

(60) Provisional application No. 60/714,071, filed on Sep. 1, 2005.

(51) Int. Cl.
*C07D 401/12* (2006.01)
*A61K 31/4725* (2006.01)

(52) U.S. Cl. ........ 514/408; 514/414; 514/423; 514/615; 546/140; 546/146; 548/465; 548/537; 564/155

(58) Field of Classification Search ..................... None
See application file for complete search history.

(56) References Cited

U.S. PATENT DOCUMENTS
5,780,589 A 7/1998 Lazarus et al.
5,811,400 A 9/1998 Schiller
2002/0161189 A1 10/2002 Lazarus et al.

FOREIGN PATENT DOCUMENTS
WO WO 03/064375 A1 8/2003

OTHER PUBLICATIONS

Arakawa et al., *Transplant. Proc.*, 24 (2), 696-697 (1992).
Arakawa et al., *Transplant. Proc.*, 25 (1), 738-740 (1993).
Arakawa et al., *Transplant.*, 53 (4), 951-953 (1992).
Arunlakshana et al., *Brit. J. Pharmacol.*, 14, 48-58 (1959).
Balboni et al., *Bioorg. Med. Chem.*, 11, 5435-5441 (2003).
Balboni et al., *J. Med. Chem.*, 45, 5556-5563 (2002).
Balboni et al., *Peptides*, 21, 1663-1671 (2000).
Bryant et al., *Biol. Chem.*, 378, 107-114 (1997).
Bryant et al., *Trends Pharmacol. Sci.*, 18, 42-46 (1998).
Capasso et al., *FEBS Lett.*, 417, 141-144 (1997).
Chappell, *Lancet*, 343, 556 (1994).
Choi et al., *J. Med. Chem.*, 40, 2733-2739 (1987).
Crescenzi et al., *Eur. J. Biochem.*, 247, 66-73 (1997).
Ermisch et al., *Physiol. Rev.*, 73, 489-527 (1993).
Flippen-Anderson et al., *J. Pept. Res.*, 49, 384-393 (1997).
Froehlich et al., *Alcohol. Clin. Exp. Res.*, 20, A181-A186 (1996).
Guerrini et al., *Bioorg. Med. Chem.*, 6, 57-62 (1998).
House et al., *Neurosci. Lett.*, 198, 119-122 (1995).
Jinsmaa et al., *Eur. J. Pharmacol.*, 509, 37-42 (2005).
Jinsmaa et al., *J. Med. Chem.*, 47, 2599-2610 (2004).
Jinsmaa et al., *J. Pharmacol. Exp. Ther.*, 309, 482-438 (2004).
Jones et al., *J. Pharmacol. Exp. Ther.*, 262, 638-645 (1992).
Kieffer et al., *PNAS USA*, 89, 12048-12052 (1992).
Lazarus et al., *Drug Disc. Today*, 3, 284-294 (1998).
Lazarus et al., *J. Biol. Chem.*, 264, 354-362 (1989).
Lazarus et al., *J. Med. Chem.*, 34, 1350-55 (1991).
Lensing et al., *Neuropsychobiol.*, 31, 16-23 (1995).
Meng et al., *PNAS USA*, 90, 9954-9958 (1993).
Menkens et al., *Eur. J. Pharm.*, 219, 346-346 (1992).
Pagé et al., *Bioorg. Med. Chem. Lett.*, 10, 167-170 (2000).
Portoghese et al., *Eur. J. Pharm.*, 146, 185-186 (1998).
Salvadori et al., *J. Med. Chem.*, 42, 5010-5019 (1999).
SALVADORi et al., *Mol. Med.*, 1, 678-689 (1995).
Santagada et al., *Bioorg. Med. Chem. Lett.*, 10, 2745-2748 (2000).
Schiller et al., *J. Med. Chem.*, 36, 3182-3187 (1993).
Schiller et al., *Peptides*, 483-486 (1994).
Schiller et al., *PNAS USA*, 89, 11871-11875 (1992).
Temussi et al., *Biochem. Biophys. Res. Commun.*, 198, 933-939 (1994).
Toth et al., *Proc. Int. Narc. Res. Conference*, 72 (2001).
Zukin et al., *PNAS USA*, 85, 4061-4065 (1988).
Bryant et al., *Biopolymers/Pept. Sci.*, 71, 86-102 (2003).
Bryant et al., *J. Med. Chem.*, 45 (25), 5506-5513 (2002).
Coupar, *Br. J. Pharmacol.*, 80, 371-376 (1983).
Evans et al., *Science*, 258, 1952-1955 (1992).
Horan et al., *J. Pharmacol. Exp. Ther.*, 265 (3), 1446-1454 (1993).
Pagé et al., *J. Med. Chem.*, 44 (15), 2387-2390 (2001).
Portoghese, *J. Med. Chem.*, 35 (11), 1927-1937 (1992).
Portoghese, *J. Med. Chem.*, 44 (14), 2259-2269 (2001).
Portoghese, *TiPS Reviews*, 10, 230-235 (1989).
Salvadori et al., *J. Med. Chem.*, 40 (19), 3100-3108 (1997).
Sasaki et al. *Bioorg. Med. Chem.*, 11, 675-678 (2003).
Weltrowska et al., *J. Peptide Res.*, 63, 63-68 (2004).

*Primary Examiner* — Zinna Northington Davis
(74) *Attorney, Agent, or Firm* — Leydig, Voit & Mayer, Ltd.

(57) ABSTRACT

The present invention relates to symmetric and asymmetric dimeric Dmt (2',6'-ditnethyl) compounds and Dmt derivative compounds with dual δ and μ opioid receptor antagonist activity. Also, the present invention provides compositions comprising these compounds and it provides methods of using these compounds.

34 Claims, 3 Drawing Sheets

DMT-DERIVATIVE COMPOUNDS AND RELATED COMPOSITIONS AND METHODS OF USE

This application is a 371 of PCT/US06/33560 filed Aug. 30, 2006 which claims benefit to Ser. No. 60/714,071 filed Sep. 1, 2005.

TECHNICAL FIELD OF THE INVENTION

The present invention relates to symmetric and asymmetric dimeric Dint (2',6'-dimethyl) compounds and Dint derivative compounds linked to amino acid residues. The Dmt dimers comprise the pharmacophore bis-Dmt-Tic (L-tyrosyl-1,2,3,4-tetrahydroisoquinoline-3-carboxylic acid)-X or bis-Dmt-X, wherein X is a diaminoalkyl spacer of variable length, optionally bonded to a pyrazinone moiety. The Dmt derivative compounds'linked to amino acid residues are modified endomorphins that comprise the following pharmacophore: Dmt-P-Xaa-F, wherein P is optionally Proline (Pro), Xaa is optionally Trptophan (Trp) or Phenylalanine (Phe) and F is Phe-NH$_2$. Another compound of the present invention is Dmt-X-Y, wherein X is a diaminoalkyl spacer having a length of 1-20 carbons, and Yaa is optionally Dmt, Tic, Phe, or another amino acid, aromatic hydrophobic ring structure or heterocyclic compound. In some embodiments the disclosed compounds are both δ- and μ-opioid receptor antagonist ligands when the N-terminal function (NH$_2$) is modified by N-alkylation with one or two methyl groups, or one or two allyl groups. The present invention also relates to compositions thereof and methods of use therefor in the antagonism of δ and μ opioid receptors.

BACKGROUND OF THE INVENTION

Endogenous opioids such as endomorphin-1 [EM-1] and endomorphin-2 [EM-2] are believed to be involved in the modulation of pain perception, in mood and behavior, learning and memory, diverse neuroendocrine functions, immune regulation and cardiovascular and respiratory function. Opioids also have a wide range of therapeutic utilities, such as treatment of opiate and alcohol abuse, neurological diseases, neuropeptide or neurotransmitter imbalances, neurological and immune system dysfunctions, graft rejections, pain control, shock and brain injuries.

There are believed to be three types of opiate receptors, namely δ, κ and μ. Genes encoding these three main receptor types now have been cloned. Sequencing of the cloned opioid receptor genes has revealed a substantial degree of amino acid homology between different receptor types (Evans et al., Science 258: 1952-1955 (1992); Kieffer et al., PNAS USA 89: 12048-12052 (1992); Meng et al., PNAS USA 90: 9954-9958 (1993); Thompson et al., Neuron 11: 903-913 (1993)), which explains the tendency of opioid receptor ligands, even those reported to be selective, to bind to more than one type of opioid receptor. Based on differences in the binding profiles of natural and synthetic ligands, subtypes of opioid receptors have been suggested, including μ1 and μ2 (Pasternak et al., Life Sci. 38: 1889-1898 (1986)) and κ1 and κ2 (Zukin et al., PNAS USA 85: 4061-4065 (1988)). Different subtypes of a given type of opioid receptor may co-exist in a single cell (Evans et al. (1992), supra; and Kieffer et al. (1992), supra).

The μ-opioid receptor in the brain appears to mediate analgesia (Kosterlitz et al., Br. J. Pharmacol. 68: 333-342 (1980)). It is also believed to be involved with other undesirable effects, such as respiratory depression (Ward et al., Soc. Neurosci. Symp. 8: 388 (abstract) (1982)), suppression of the immune system (Plotnikoff et al., Enkephalins and Endorphins: Stress and the Immune System, Plenum Press, NY (1986); Yalya et al., Life Sci. 41: 2503-2510 (1987)) and addiction (Roemer et al., Life Sci. 27: 971-978 (1981)). Its side effects in the periphery include inhibition of intestinal motility (Ward et al., Eur. J. Pharmacol. 85: 163-170 (1982)) and secretion in the small intestine (Coupar, Br. J. Pharmacol. 80: 371-376 (1983)).

δ-Opioid receptors also mediate analgesic but are not involved in addiction. They may have an indirect role in immune suppression and act in concert with μ-opioid receptors.

There appears to be a single binding site for agonists and antagonists in the ligand-binding domain of δ receptors. Thus, the "message domain" of δ-agonists and δ-antagonists probably presents a similar low energy conformer in order to fit the receptor cavity. The minimum size of that "message domain" constitutes the dimensions of a dipeptide (Temussi et al., Biochem. Biophys. Res. Commun. 198: 933-939 (1994); Mosberg et al., Lett. Pept. Sci. 1: 69-72 (1994); and Salvadori et al., J. Med. Chem. 42: 3100-3108 (1997)), which has a specific spatial geometry in solution (Bryant et al., Trends Pharmacol. Sci. 18: 42-46 (1998); Bryant et al., Biol. Chem. 378: 107-114 (1997); Crescenzi et al., Eur. J. Biochem. 247: 66-73 (1997); and Guerrini et al., Bioorg. Med. Chem. 6: 57-62 (1998)) as seen in the crystallographic evidence for TIPP analogues (Flippen-Anderson et al., J. Pept. Res. 49: 384-393 (1997)) and N,N(Me)$_2$-Dmt-Tic-OH (Bryant et al. J. Med. Chem. 45, 5506-5513 (2002).

The Dmt-Tic pharmacophore represents a distinct class of δ-opioid antagonists (Salvadori et al., Mol. Med. 1: 678-689 (1995); Bryant et al. (1998), supra; Lazarus et al., Drug Dev. Today 284-294 (1998); Bryant et al., Biopolymers/Pept. Sci. 71, 86-102 (2003)). Observations of differences between the δ opioid receptor binding of Dmt-Tic peptides and their Tyr-Tic cognates (Salvadori et al. (1995), supra; Lazarus et al. (1998), supra; and Lazarus et al., Int'l Symp. on Peptide Chem. and Biol., Changchung, PRC (1999)) indicates that Dmt assumes a predominant role in the alignment or anchoring of the peptide within δ, μ and κ opioid receptor binding sites (Bryant et al. (1998), supra; and Bryant et al. (1997), supra; Crescenzi et al. (1997), supra; and Guerrini et al. (1998), supra) or affects the conformation of the dipeptide antagonists in solution (Bryant et al. (1997), supra; and Crescenzi et al. (1997), supra). Furthermore, observations of differences between the spectra of activity exhibited by the Tyr-Tic cognates of certain Dmt-Tic peptides (Schiller et al., PNAS USA 89: 11871-11875 (1992); Schiller et al., J. Med. Chem. 36: 3182-3187 (1993); Schiller et al., Peptides Hodges and Smith, eds., ESCOM (1994); pp. 483-486; Temussi et al. (1994), supra; Mosberg et al. (1994), supra; Salvadori et al. (1995), supra; Lazarus et al. (1998), supra; and Lazarus et al. (1999), supra) and the corresponding Dmt-Tic peptides suggests that the C-terminal "address" portion of the peptide can influence the "message domain."

Recently, cyclic peptides and di- and tri-peptides comprising the pharmacophore Dmt-Tic have been developed and have been shown to exhibit high selectivity, affinity and potency for the δ-opioid receptor. Such peptides have been shown to function as agonists, partial agonists, antagonists, partial antagonists or mixed antagonists/agonists for opioid receptors (see Lazarus et al., U.S. Pat. No. 5,780,589, and Schiller, U.S. Pat. No. 5,811,400).

A variety of modifications to the Tic residue differentially changes receptor selectivity, including alterations in its electronic configuration and chirality, as well as its replacement by heteroaliphatic/heteroaromatic nuclei or D-Phe (Santagada et al., *Med. Chem. Lett.*, 10, 2745-2748 (2000); Pagé et al., *Bioorg. Med. Chem. Lett.*, 10, 167-170 (2000); Salvadori et al., *Mol. Med.*, 1: 678-689 (1995); Balboni et al., *Peptides*, 21: 1663-1671 (2000); and Capasso et al., *FEBS Lett.*, 417: 141-144 (1997)). Changes wrought by altering the distance to a third aromatic center at the C-terminus by an interposed sequence, a spacer or linker ("X"), induces profound changes in the affinity, selectivity and bioactivity of a ligand (Capasso et al., *FEBS Lett.*, 417: 141-144 (1997); Salvadori et al., *J. Med. Chem.*, 42: 5010-5019 (1999); Pagé et al., *J. Med. Chem.*, 44: 2387-2390 (2001); Balboni et al., J. Med. Chem. 45, 5556-5563 (2002)).

Moreover, it is known that tail-to-tail condensation of pharmacophores such as dimeric dermorphin analogues (Lazarus et al., J. Biol. Chem. 264, 354-362 (1989)), biphalin [Tyr-D-Ala-Gly-Phe-NH—)$_2$]—a dimericenkephalin analogue, and norbinaltrophimine (norBNI)—a dimer of naltrexone derivatives, significantly improves opioid receptor affinity and altered biological activity (Portoghese et al., *Trends Pharmacol. Sci.*, 10: 230-235 (1989); Portoghese et al., *J. Med. Chem.*, 35: 1927-1937 (1992); Portoghese et al., *J. Med. Chem.*, 44: 2259-2269 (2001); Lipkowski et al., *Peptides*, 3: 697-700 (1982); Lazarus et al., *J. Biol. Chem.*, 264: 354-362 (1989); Horan et al., *J. Pharmacol. Exp. Ther.*, 265: 1446-54 (1993); Weltrowska et al., *J. Peptide Res.*, 63: 63-68 (2004); Portoghese et al., *Life Sci.*, 40: 1287-1292 (1987)).

The uniqueness of the δ receptor has led to the use of moderately δ-selective alkaloid antagonists in clinical trials, such as for the amelioration of the effects of alcoholism (Froehlich et al., *Alcohol. Clin. Exp. Res.* 20: A181-A186 (1996)), the treatment of autism (Lensing et al., *Neuropsychobiol.* 31: 16-23 (1995)), and Tourette's syndrome (Chappell, *Lancet* 343: 556 (1994)). The δ-opiate antagonist naltrindole (Portoghese et al., *Eur. J. Pharm.* 146: 185-186 (1998)) has been shown to inhibit the reinforcing properties of cocaine (Menkens et al., *Eur. J. Pharm.* 219: 346-346 (1992)), to moderate the behavioral effects of amphetamines (Jones et al., *J. Pharmacol. Exp. Ther.* 262: 638-645 (1992)), and to suppress the immune system (Jones et al. (1992), supra) for successful organ transplantation (House et al., *Neurosci. Lett.* 198: 119-122 (1995)) in animal models (Arakawa et al., *Transplant Proc.* 24: 696-697 (1992); Arakawa et al., *Transplant* 53: 951-953 (1992); and Arakawa et al., *Transplant. Proc.* 25: 738-740 (1993)). The same effects also have been shown for 7-benzylspiroindanylnaltrexone (Lipper et al., *Eur. J. Pharmacol.* 354: R3-R5 (1998)).

The intractable membrane barriers, such as the blood-brain barrier (BBB), must be circumvented in order for peptide antagonists to express activity in vivo (Ermisch et al., *Physiol. Rev.* 73: 489-527 (1993)). The requisite physicochemical properties of compounds capable of passing through this barrier include low molecular weight (<800 Da) and high octanol-water coefficient characteristics.

In view of the above, the present invention provides more potent μ-opioid antagonists and δ-opioid antagonists, whereby the antagonists have a high dual binding affinity and biological activity toward δ-opioid and μ-opioid receptors, providing a means to simultaneously down-regulate two independent opioid receptors, and whereby the antagonists can pass through the blood-brain barrier following systemic or oral administration. Also, the present invention provides compositions comprising these compounds and it provides methods of using these compounds as therapeutic agents in the treatment of tolerance, alcohol dependency, and drug addiction.

The present invention also transforms selective μ-opioid receptor agonists into potent μ-opioid receptor antagonists. Also, the present invention provides compositions comprising these compounds and it provides methods of using these compounds as therapeutic agents in the treatment of drug tolerance, alcohol dependency, and drug addiction.

These and other objects of the present invention, as well as additional inventive features, will be apparent to the ordinarily skilled artisan from the detailed description provided herein.

BRIEF SUMMARY OF THE INVENTION

Compounds of the present invention, which are μ-opioid receptor and δ-opioid receptor antagonists, are capable of down regulating both receptor types. The dual antagonist property of these compounds in a single compound is highly beneficial. Specifically, the present invention comprises compounds of the pharmacophore H-Dmt-Tic-NH—(CH$_2$)n-NH-Tic-Dmt-H or H-Dmt-NH—(CH$_2$)$_n$-pyrazinone-(CH$_2$)$_m$—NH-Dmt-H, wherein the diaminoalkyl group ("n" or "m") is of variable length and where "n" may or may not equal "m." Also, the present invention provides a composition comprising these compounds and it provides methods of using these compounds.

The present invention further comprises compounds of the pharmacophore Dmt-Tic-3-NH—(CH$_2$)n-6-NH—(CH$_2$)m-2(1H)-pyrazinone-Tic-Dmt or Dmt-3-NH—(CH$_2$)n-6-NH—(CH$_2$)m-2(1H)-pyrazinone-Dmt, wherein each aminoalkyl is of variable length ("n", "m"), and wherein the aminoalkyl groups are bonded to the pyrazinone moiety, preferably at the 3 and 6 carbon, respectively. Also, the present invention provides a composition comprising these compounds and it provides methods of using these compounds.

The present invention further provides for the endomorphin compounds H-Dmt-Pro (Proline)-Trp (Tryptophan)-Phe (Phenylalanine)-NH$_2$ ("[Dmt[1]] EM-1") and H-Dmt-Pro-Phe-Phe-NH$_2$ ("[Dmt[1]] EM-2") and derivatives thereof. Also, the present invention provides a composition comprising these compounds and it provides methods of using these compounds.

The present invention further provides for Dmt-Tic derivatives linked to amino acid residues comprising the pharmacophore Dmt-Tic-NH—(CH$_2$)n-NH-Yaa, wherein Yaa is Dmt, Tic, Phenylalanine, or another amino acid and the diaminoalkyl group is of variable length ("n"). Also, the present invention provides a composition comprising these compounds and it provides methods of using these compounds.

DETAILED DESCRIPTION OF THE INVENTION

Figure 1:
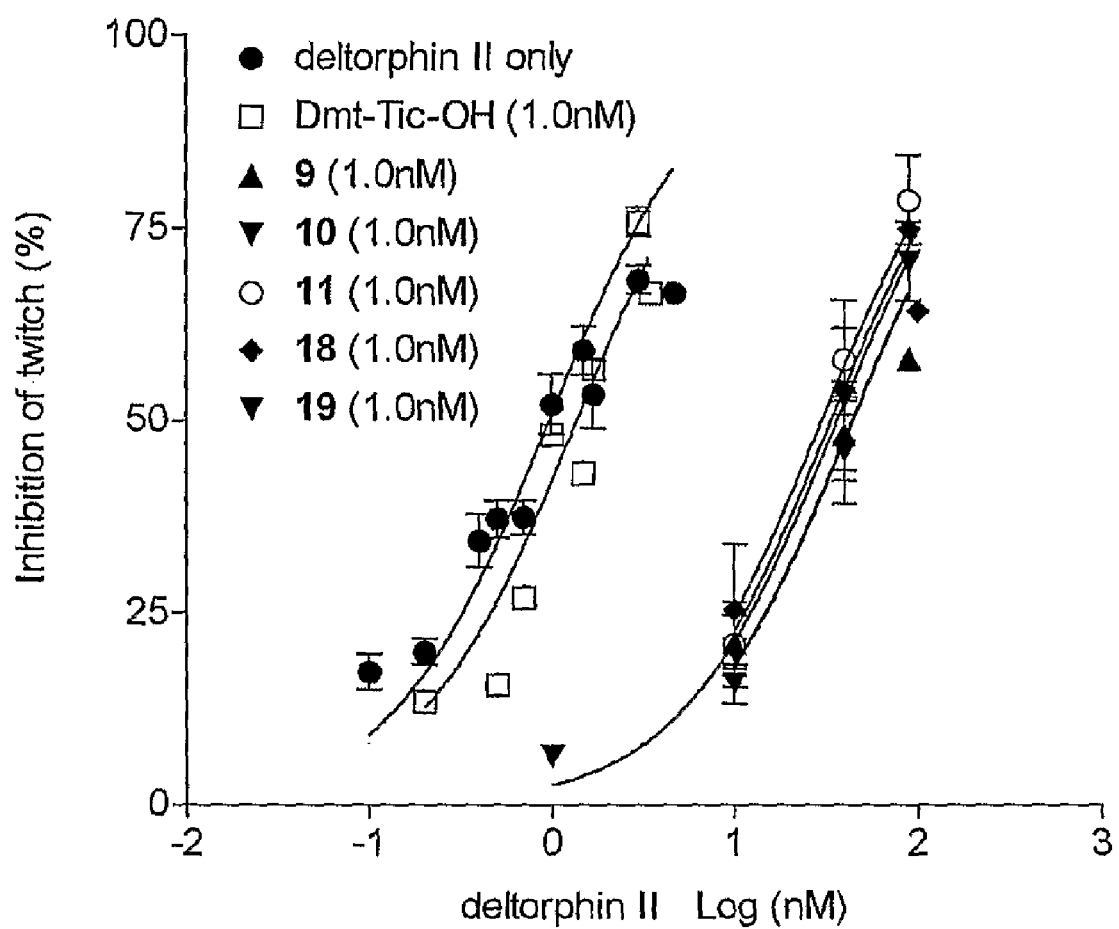
FIG. 1 illustrates the antagonism of inventive Dmt-Tic analog compounds 9, 10, 11, 18, 19 in a MVD bioassay.

The present invention provides a compound of formula I:

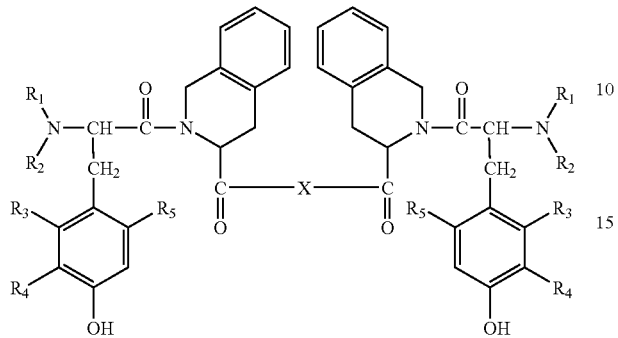

(I)

wherein $R_1$ and $R_2$ are the same or different and each of $R_1$ and $R_2$ is H, or $CH_3$;
$R_3$ and $R_5$ are the same or different and each of $R_3$ and $R_5$ is H, $CH_3$, or $C_2H_5$;
$R_4$ is H, or $CH_3$;
X is a spacer consisting of NH—$(CH_2)$n-NH, wherein n is from 1 to about 20; or
3-NH—$(CH_2)$n-6-NH—$(CH_2)$m-2(1H)-pyrazinone, wherein "n" and "m" are the same or different and each of n and m is from 1 to about 20.

The present invention further provides a compound of formula II:

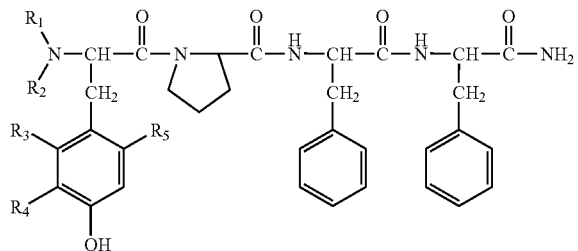

(II)

wherein $R_1$ is H, or an allyl group;
$R_2$ is an allyl group;
$R_3$ and $R_5$ are the same or different and each of $R_3$ and $R_5$ is H, $CH_3$, or $C_2H_5$; and
$R_4$ is H, $CH_3$ The present invention further provides a compound of formula (III):

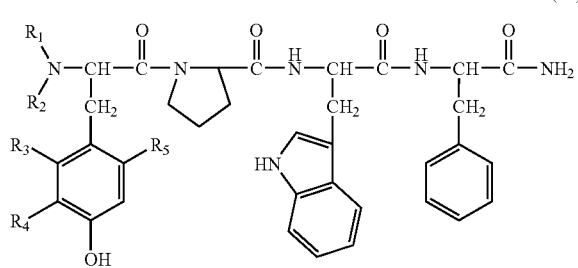

(III)

wherein $R_1$ is H, or an allyl group;
$R_2$ is an allyl group;
$R_3$ and $R_5$ are the same or different and each of $R_3$ and $R_5$ is H, $CH_3$, or $C_2H_5$; and
$R_4$ is H, or $CH_3$ The present invention further provides a compound of formula IV:

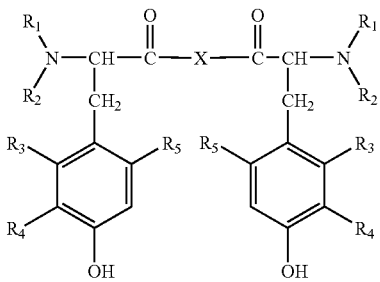

(IV)

wherein $R_1$ is H, or an allyl group;
$R_2$ is an allyl group;
$R_3$ and $R_5$ are the same or different and each of $R_3$ and $R_5$ is H, $CH_3$, or $C_2H_5$;
$R_4$ is H, or $CH_3$;
X is a spacer consisting of NH—$(CH_2)$n-NH, wherein n is from 1 to about 20; or 3-NH—$(CH_2)$n-6-NH—$(CH_2)$m-2 (1H)-pyrazinone, wherein n and m are the same or different and each of n and m is from 1 to about 20.

The present invention further provides a compound of formula V:

(V)

wherein $R_1$ and $R_2$ are the same or different and each of $R_1$ and $R_2$ is H, or $CH_3$;
$R_3$ and $R_5$ are the same or different and each of $R_3$ and $R_5$ is H, $CH_3$, or $C_2H_5$;
$R_4$ is H, or $CH_3$;
n is 1-20; and
Yaa is Dmt, Tic, Phe, another amino acid.

In specific embodiments of the inventive compounds (I, IV, and V), "n" and "m" can be the same or different and each of "n" and "m" is from 1 to about 20, and preferably, from 1 to about 10, and more preferably, from 1 to about 8.

Also provided by the present invention is a composition comprising at least one of the above-described compounds and a carrier.

The present invention further provides a method of treating a mammal in need of an antagonist of a µ-opioid receptor. The method comprises administering at least one of the above-described compounds in an amount sufficient to antagonize a μ-opioid receptor in said mammal as measured by the GPI (ileum muscle preparation from Hartley strain Guinea Pig Intestine) bioassay.

In another embodiment, the present invention provides a method of treating a mammal in need of an antagonist of a δ-opioid receptor. The method comprises administering at least one of the above-described compounds in an amount sufficient to antagonize a δ-opioid receptor in said mammal as measured by the MVD (mouse vas deferens) bioassay.

In yet another embodiment, the present invention provides a method of treating a mammal in need of a dual antagonist that has μ-opioid and δ-opioid bioactivity. The method comprises administering at least one of the above-described compounds in an amount that antagonizes both the μ-opioid receptor and the δ-opioid receptor as measured by the GPI and MVD bioassays, respectively.

The present inventive compounds can be synthesized, in part, using standard methods known to those of ordinary skill in the art. See, for example, *Modern Techniques of Peptide and Amino Acid Analysis*, John Wiley & Sons (1981); Bodansky, *Principles of Peptide Synthesis*, Springer Verlag (1984); Lazarus et al., *Drug Disc. Today*, 3: 284-294 (1998)). Specific examples of the synthesis of the inventive compounds are described in the Examples herein.

The present inventive compounds exhibit high binding affinity for both δ-opioid receptors and μ-opioid receptors resulting in moderate δ-receptor selectivity with high δ-opioid receptor antagonism in all Dmt-Tic analog compounds (8-14, and 18-22) such that their $K_i$ values are less than 0.1 nM, respectively while δ and μ opioid agonism, as measured by the MVD and GPI bioassays, is essentially absent as indicated by $IC_{50}$ values of greater than 1 μM, respectively. The enhanced opioid mediated characteristics of the inventive compounds rely, in part, on the presence of a spacer ("X") incorporated within the inventive dimeric and non-dimeric Dmt-Tic analog compounds. The type of spacer is not narrowly critical and preferably is diaminoalkyl, or symmetric or asymmetric 3,6-diaminoalkyl-2(1H)-pyrazinone moieties, with the proviso that the spacer is not a single methylene group. Furthermore, incorporation of an alkyl-pyrazinone spacer in the inventive compounds, such as those described in the formulas and as exemplified by compound 22 described in the Examples, allows the compounds to pass through the blood-brain barrier when administered to a mammal by injection or oral pharmaceutical formulation (Jinsmaa et al., *J. Pharmacol. Exp. Ther.* 309: 1-7 (2004); Jinsmaa et al., J. Med. Chem. 47: 2599-2610 (2004)).

In the present inventive compounds, it is believed that the incorporation of the spacer is partially responsible for the simultaneous, dual δ- and μ-opioid antagonism. In addition to the spacer, it is believed that the superior antagonistic activity of the inventive compounds, such as compounds 21, and 22, is a result of modification to the N-terminus of the Dmt-Tic analog compounds, for example, with N,N-dimethylation of the N-terminus. The N-terminus modification of the inventive compounds results in enhanced μ-opioid antagonist activity without altering the inventive compounds' characteristic δ-opioid antagonist activity, whereby the present invention represents a novel single opioid ligand containing potent, dual δ- and μ-opioid antagonist bioactivities.

The inventive Dmt-Tic analog compounds can undergo further modifications including N,N-dimethylation, as described above, N-terminal modifications with alkyl substitutions, replacement of Tic by heteroaliphatic, heteroaromatic nuclei or D-Phe, C-terminus alterations of Tic with substituents containing hydrophobic groups, or the addition of a third aromatic center with or without inserting interposing linkers, providing compounds with enhanced opioid antagonist activity.

In another embodiment of the inventive compounds, these compounds can simultaneously down-regulate two independent opioid receptors (δ- and μ-) for use in the treatment of tolerance, alcohol dependency, and drug addiction.

In yet another embodiment of the invention, the inventive compounds comprise selective μ-opioid receptor agonist ligands that are transformed to μ-opioid receptor antagonists. Selective μ-opioid receptor agonist ligands include, but are not limited to, endomorphin-1 ("EM-1") and endomorphin-2 ("EM-2"). Modification of a selective μ-opioid receptor ligand with Dmt[1] enhances the bioactive properties of the molecules in question and modification of its N-terminal amine transforms the μ-opioid agonist ligand to a μ-opioid antagonist compound (e.g. [Dmt[1]] EM-2). For example, Dmt[1]-derivatized endomorphin with N-allylation (e.g. N-allyl-[Dmt[1]] EM-2) provides compounds having high affinity for μ-opioid receptors and enhanced μ-opioid antagonist activity relative to non-allylated compounds. The N-allylation of the inventive compounds can be via incorporation of a monoallyl or a diallyl, and preferably, the N-terminus of the [Dmt[1]] EM-1 and [Dmt[1]] EM-2 derivatives is monoallylated with an allyl group. Bioactivity assays of the monoallylated inventive compounds illustrate the enhanced μ-opioid antagonism of these compounds, relative to diallylated [Dmt[1]] EM-2 derivative compounds.

A further aspect of the inventive Dmt[1]-derivatized endomorphin compounds, such as, for example, compound 33, is the ability of the compounds to inhibit morphine-induced analgesia in mice post intracerebroventricular administration.

In another embodiment of the inventive Dmt[1]-derivatized endomorphin compounds, these compounds are useful in the treatment of tolerance, alcohol dependency, drug and morphine addiction associated with μ-opioid bioactivity.

The level of opioid antagonist activity of the inventive compounds is set forth, in part, in the Examples herein. Additionally, conventional techniques known to those of ordinary skill in the art can be used to make such determinations. Examples of such techniques include, but are not limited to, the mouse vas deferens (MVD) bioassay of δ-opioid bioactivity and the guinea pig ileum (GPI) bioassay of μ-opioid activity as described in the Examples. Examples of in vivo studies include, but are not limited to, the tail flick test (Harris et al., *J. Pharmacol. Meth.* 20: 103-108 (1988); and Sing et al., *P.A. Amber* (v. 3.0. rev. A), Dept. Pharm. Chem., University of California, San Francisco (1988)) and hot-plate test.

The present invention further provides a composition comprising at least one of the above compounds. Desirably, the composition comprises at least one carrier, which is preferably a pharmaceutically acceptable carrier, diluent or vehicle. Also, desirably, the composition is formulated for human administration produced by cGMP methods (current Good Manufacturing Process) to ensure consistency in the formulation and final product. Pharmaceutically acceptable carriers are well-known to those of ordinary skill in the art, as are suitable methods of administration. The choice of carrier will be determined, in part, by the particular method used to administer the composition. One of ordinary skill in the art will also appreciate that various routes of administering a composition are available, and, although more than one route can be used for administration, a particular route can provide a more immediate and more effective reaction than another route. Accordingly, there are a wide variety of suitable formulations of compositions that can be used in the present inventive methods.

A compound of the present invention can be made into a formulation suitable for parenteral administration, preferably intraperitoneal administration, or dural administration. Such a formulation can include aqueous and nonaqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit dose or multi-dose sealed containers, such as ampules and vials, and can be stored in a freeze-dried (lyophilized) condition requiring only the addition of the sterile liquid carrier, for example, water, for injections, immediately prior to use. Extemporaneously injectable solutions and suspensions can be prepared from sterile powders, granules, and tablets, as described herein.

A formulation suitable for oral administration can consist of liquid solutions, such as an effective amount of the compound dissolved in diluents, such as water, saline, or fruit juice; capsules, sachets or tablets, each containing a predetermined amount of the active ingredient, as solid or granules; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Furthermore, time release encapsulation methods are tailored in order to deliver the active ingredient over a specified time period between repeated administrations as determined by clinical trials.

Similarly, a formulation suitable for oral administration can include lozenge forms, which can comprise the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels, and the like containing, in addition to the active ingredient, such carriers as are known in the art.

An aerosol formulation suitable for administration via inhalation also can be made. The aerosol formulation can be placed into a pressurized acceptable propellant, such as dichlorodifluoromethane, propane, nitrogen, and the like.

A formulation suitable for topical application can be in the form of creams, ointments, or lotions.

A formulation for rectal administration can be presented as a suppository with a suitable base comprising, for example, cocoa butter or a salicylate. A formulation suitable for vaginal administration can be presented as a pessary, tampon, cream, gel, paste, foam, or spray formula containing, in addition to the active ingredient, such carriers as are known in the art to be appropriate.

Any of the above compositions can further comprise one or more other active agents. Alternatively, any of the above compositions can be administered, by the same or different route, in combination with another composition comprising one or more other active agents, either simultaneously or sequentially in either order sufficiently close in time to realize the benefit of such co-administration.

The dose administered to a mammal, particularly a human, in the context of the present invention should be sufficient to effect a therapeutic response in the individual over a reasonable time frame. The dose will be determined by the potency of the particular compound employed for treatment, the severity of any condition to be treated, as well as the body weight and age of the individual. The size of the dose also will be determined by the existence of any potential adverse side effects that may accompany the use of the particular compound employed. It is always desirable, whenever possible, to keep adverse side effects to a minimum. Adverse side effects are studied in advance with the use of animal models based on pharmacokinetic principles.

The dosage can be in unit dosage form, such as a tablet or capsule. The term "unit dosage form" as used herein refers to physically discrete units suitable as unitary dosages for human and animal subjects, each unit containing a predetermined quantity of a compound, alone or in combination with other active agents, calculated in an amount sufficient to produce the desired effect in association with a pharmaceutically acceptable diluent, carrier, or vehicle. The specifications for the unit dosage forms of the present invention depend on the particular embodiment employed and the effect to be achieved, as well as the pharmacodynamics associated with each compound in the host. The dose administered should be an effective amount, i.e., an amount effective to antagonize a $\delta$-opioid receptor and/or a $\mu$-opioid receptor as desired.

Since the "effective amount" is used as the preferred endpoint for dosing, the actual dose and schedule can vary, depending on interindividual differences in pharmacokinetics, drug distribution, and metabolism. The "effective amount" can be defined, for example, as the blood or tissue level desired in the patient that corresponds to a concentration of one or more compounds according to the invention. The "effective amount" for a given compound of the present invention also can vary when the composition of the present invention comprises another active agent or is used in combination with another composition comprising another active agent.

One of ordinary skill in the art can easily determine the appropriate dose, schedule, and method of administration for the exact formulation of the composition being used, in order to achieve the desired "effective amount" in the individual patient. One skilled in the art also can readily determine and use an appropriate indicator of the "effective amount" of the compound of the present invention by pharmacological endpoint analysis.

Further, with respect to determining the effective amount in a patient, suitable animal models are available and have been widely implemented for evaluating the in vivo efficacy of such compounds. These models include the tail-flick test and hot-plate test (see, e.g., U.S. Pat. No. 5,780,589). In vitro models are also available, examples of which are set forth in the Examples herein.

Generally, an amount of a present inventive compound up to about 50 mg/kg body weight, preferably from about 10 mg/kg body weight to about 50 mg/kg body weight is preferred, especially from about 10 mg/kg body weight to about 20 mg/kg body weight. In certain applications, multiple daily doses are preferred. Moreover, the number of doses will vary depending on the means of delivery and the particular compound administered.

The following examples serve to illustrate further the present invention and are not intended to limit its scope in any way.

Nomenclature as established by the IUPAC-IUB Commission on Biochemical Nomenclature (*J. Biol. Chem.* 260: 1442 (1985)) will be used herein. In addition, the following symbols and abbreviations will be used:

Ac$_2$O: acetic anhydride
AcOEt: ethyl acetate
BBB: blood-brain barrier
Boc: tert-butyloxycarbonyl
BSA: bovine serum albumin
Dab: diaminobutane
Dap: diaminopropane
DALDE: [D-Ala,$^2$ D-Leu$^5$]enkephalin
DAMGO: [D-Ala$^2$,N-Me-Phe$^4$,Gly-ol$^5$]enkephalin
deltorphin II: Tyr-D-Ala-Phe-Glu-Val-Val-Gly-NH$_2$
DIPEA: diisopropylethylamine
DMF: N,N-dimethylformamide
DMSO: dimethylsulfoxide
Dmt: 2',6'-dimethyl-L-tyrosine
Fmoc: 9-Fluorenylmethoxycarbonyl
EM-1: endomorphin-1 (Tyr-Pro-Trp-Phe-NH$_2$)
EM-2: endomorphin-2 (Tyr-Pro-Phe-Phe-NH$_2$)
Et: ethyl (C$_2$H$_5$)
Et$_2$O: diethyl ether
GPI: guinea pig ileum (μ receptor bioassay)
IBCF: isobutyl chloroformate
IC$_{50}$: concentration required for 50% inhibition of the electrically induced contraction in muscle derived from a dose-response curve
Lys: lysine
Me: methyl
MVD: mouse vas deferens (δ specific bioassay)
NaBH$_3$CN: sodium cyanoborohydride
NMR: nuclear magnetic resonance
OMe: methyl ester
Orn: ornithine
PyBOP: benzoltriazol-1-yloxytrispyrrolidinophosphonium hexafluorphosphate
RP-HPLC: reverse phase high performance liquid chromatography
K$_e$: the antilog of pA$_2$ in molar concentration
pA$_2$: negative log of the molar concentration required to double the agonist concentration to achieve the original response
tBu: tert-butyl
TFA: trifluoroacetic acid
Tic: 1,2,3,4-tetrahydroisoquinoline-3-carboxylic acid
TLC: thin layer chromatography
Tyr-OMe: Tyrosine methyl ester
Z: benzyloxycarbonyl Example 1

This example illustrates the general procedure for synthesis of compounds 1-7 described below. 3,6-Bis(Z-aminoalkyl)-2(1H)-pyrazinone (0.27 mmol) was stirred in 25% HBr/AcOH (1.88 mL, 7.8 mmol) with an ice bath for 10 min then room temperature for 3 hr. The resulting amine was precipitated with ether and dried in vacuo. The precipitate was dissolved in DMF (10 mL) containing DIPEA (237 ml, 1.36 mmol), to which Boc-Dmt-Tic-OH (277 mg, 0.593 mmol) and PyBop (324 mg, 0.62 mmol) were added. The solution was first stirred in an ice hath for 10 min, then at room temperature for 4 h. After removal of the solvent in vacuo, the residue was extracted with AcOEt, which was washed with 10% citric acid (3×10 mL), 5% NaHCO$_3$ (3×10 mL), and saturated aqueous NaCl solution (3×15 mL), and dried over NaSO$_4$. After filtration, the solvent was evaporated in vacuo, and the crude compound was purified by silica gel chromatography and precipitated with ether.

Compound 1—3,6-Bis(Boc-Dmt-Tic-NH-methyl)-2 (1H)-pyrazinone (1)

Starting from 3,6-bis(Z—NH—CH$_2$)-2(1H)-pyrazinone (70 mg, 0.16 mmol), the crude compound was purified by silica gel chromatography (2.8 cm×33 cm; AcOEt: MeOH=13:1). Yield 144 mg (84.2%); mp 165-167° C.; R$_{f3}$=0.57; [α]$_D^{25}$ +2.49°(c=0.45, MeOH). Anal. Calcd for C$_{59}$H$_{72}$N$_8$O$_{11}$ 2.2H$_2$O: C, 63.9; H, 6.89; N, 10.1. Found: C, 63.8; H, 6.90; N, 10.5. $^1$H NMR (400 MHz, CDCl$_3$): 12.59 (s, 1H), 8.99 (d, 1H, J=9.11 Hz), 8.05 (s, 1H), 7.59 (s, 1H), 7.3-7.0 (m, 8H), 7.85-5.85 (m, 4H), 5.80 (d, 0.93H, J=5.21 Hz), 5.48 (d, 0.93H, J=8.79 Hz), 5.36-5.20 (m, 1H), 5.20-4.96 (m, 3.88H), 4.86-4.52 (m, 3.2H), 4.48-4.33 (m, 1.89H), 4.19 (d, 0.95H, J=17.86 Hz), 3.97-3.72 (m, 1.93H), 3.60 (d, 0.93H, J=15.55 Hz), 3.28-2.86 (m, 5.22H), 2.71 (d, 0.93H, J=11.56 Hz), 2.63-1.85 (m, 16H), 1.5-0.5 (m, 18H). $^{13}$C NMR (CDCl$_3$): 173.04, 172.96, 171.45, 169.91, 156.88, 156.74, 155.83, 155.04, 154.59, 151.72, 138.68, 133.21, 132.72, 130.91, 130.73, 129.82 (16q), 129.51, 128.55, 128.46, 126.97, 126.62, 126.54, 126.41, 126.30, 126.11 (9t), 123.60, 122.98 (2q), 116.58, 115.75 (2t), 81.24, 80.11 (2q), 55.77, 51.20, 50.60, 48.83 (4t), 46.34, 46.29, 45.11, 44.04, 40.70, 37.09, 34.27, 31.68, 29.48 (9t), 28.38 (t), 28.15 (s), 27.49 (t), 26.46, 26.38 (2s), 20.48, 19.90, 18.40 (3p).

Compound 2—3,6-Bis(Boc-Dmt-Tic-NH-ethyl)-2 (1H)-pyrazinone (2)

Starting from 3,6-bis[Z—NH—(CH$_2$)$_2$]-2(1H)-pyrazinone (125 mg, 0.27 mmol), the crude compound was purified by silica gel chromatography (2.6 cm×34 cm; AcOEt: MeOH=20:1). Yield 186 mg (62.9%); mp 177-178° C.; R$_{f2}$=0.56; [α]$_D^{25}$ -21.2° (c=0.38, MeOH). Anal. Calcd for C$_{61}$H$_{76}$N$_8$O$_{11}$ H$_2$O: C, 65.6; H, 6.99; N, 10.0. Found: C, 65.6; H, 6.77; N, 10.1. $^1$H NMR (400 MHz, CDCl$_3$): 8.9 (br, 1H), 7.8-7.4 (m, 1H), 7.2-6.73 (m, 8H), 6.73-6.28 (m, 4H), 5.7-5.38 (m, 1.7H), 5.38-4.85 (m, 3.3H), 4.85-4.15 (m, 3H), 4.0-3.6 (m, 2.3H), 3.6-2.36 (m, 11H), 2.36-1.65 (m, 21H), 1.5-1.15 (19.6H). $^{13}$C NMR (CDCl$_3$): 174.01, 173.96, 173.54, 173.17, 170.54, 170.16, 170.0, 169.89, 156.65, 156.50, 156.28, 155.98, 155.80, 155.50, 155.13, 155.03, 139.16, 138.82, 133.81, 133.72, 133.28, 132.62, 131.28, 131.23 (24q), 128.52, 128.44, 128.01, 127.96, 127.89, 127.53, 127.09, 127.05, 126.86, 126.08, 125.83 (11t), 124.45, 124.05, 123.92, 123.22 (4q), 116.04, 115.99, 115.66 (3t), 80.77, 80.17, 80.08, 80.02 (4q), 55.77, 54.60, 50.37, 49.32 (4t), 45.70, 44.04, 37.73, 37.66, 36.72, 36.58, 33.31, 30.75, 30.21 (9s), 28.39, 28.37 (2p), 20.43, 20.28, 19.96, 18.0 (4p).

Compound 3—3,6-Bis(Boc-Dmt-Tic-NH-propyl)-2 (1H)-pyrazinone (3)

Starting from 3,6-bis[Z—NH—(CH$_2$)$_3$]-2(1H)-pyrazinone (132 mg, 0.27 mmol), the crude compound was purified by silica gel chromatography (2.6 cm×34 cm; AcOEt: MeOH=20:1). Yield 157 mg (51.8%); mp 165-166° C.; R$_{f2}$=0.56; [α]$_D^{25}$ -9.37° (c=0.36, MeOH). Anal. Calcd for C$_{63}$H$_{80}$N$_8$O$_{11}$ 1.5H$_2$O: C, 65.6; H, 7.20; N, 9.72. Found: C, 65.6; H, 6.84; N, 9.74. $^1$H NMR (400 MHz, CDCl$_3$): 8.9 (br, 1H), 8.0-8.5 (m, 1H), 7.15-6.7 (m, 8H), 6.7-6.4 (m, 4H), 5.75-5.3 (m, 2H), 5.3-4.8 (m, 3.4H), 4.8-4.3 (m, 3.0H), 4.0-3.7 (m, 1.6H), 3.5-2.85 (m, 10.5H), 2.85-1.6 (m, 20.6H), 1.6-1.1 (m, 22.3H). $^{13}$C NMR (CDCl$_3$): 173.91, 173.70, 173.19, 171.02, 170.85, 169.72, 169.52, 156.45, 156.23, 155.93, 155.71, 155.69, 155.54, 155.21, 155.10, 138.96, 138.81, 138.68, 133.58, 133.54, 133.46, 132.87, 131.63, 131.44, 131.12, 131.07 (26q), 128.47, 127.68, 127.55, 127.34, 126.95, 126.74, 126.70, 126.66, 126.21, 125.87 (10t), 124.03, 123.83, 123.03 (3q), 115.85, 115.79, 115.60, 115.34 (4t), 80.68, 80.63, 80.18, 80.04 (4q), 55.96, 54.16, 50.79, 49.42 (4t), 45.59, 44.65, 38.95, 38.02, 33.47, 31.95, 31.36, 31.16 (8s), 28.37, 28.33 (2p), 26.84, 25.70 (2s), 20.43, 20.38, 19.97, 17.84 (4p).

Compound 4—3,6-Bis(Boc-Dmt-Tic-NH-butyl)-2 (1H)-pyrazinone (4)

Starting from 3,6-bis[Z—NH—(CH$_2$)$_4$]-2(1H)-pyrazinone (130 mg, 0.25 mmol), the crude compound was purified with silica gel chromatography (2.8 cm×36 cm; CHCl$_3$:MeOH=20:1). Yield 226 mg (78.5%); mp 162-164° C.; R$_{f3}$=0.62; [α]$_D^{25}$ −4.1°(c=0.38, MeOH). Anal. Calcd for C$_{63}$H$_{80}$N$_8$O$_{11}$·1.7H$_2$O: C, 65.9; H, 7.38; N, 9.46. Found: C, 65.8; H, 7.25; N, 9.44. $^1$H NMR (400 MHz, CDCl$_3$): 7.6-7.4 (m, 0.91H), 7.2-6.7 (m, 8.31H), 6.7-6.35 (m, 4H), 5.65-5.4 (m, 1.78H), 5.24-4.83 (m, 3.35H), 4.83-4.3 (m, 3.59H), 4.05-3.7 (m, 1.89H), 3.5-2.75 (m, 10.83H), 2.75-1.7 (m, 21.92H), 1.65-0.6 (m, 26.28H). $^{13}$C NMR (CDCl$_3$): 174.0, 173.93, 173.35, 173.23, 170.81, 170.44, 170.0, 169.50, 156.90, 156.55, 156.04, 155.73, 155.36, 15.17, 138.99, 138.87, 138.73, 138.58, 133.76, 133.68, 131.25, 131.10, 131.55, 131.27 (24q), 128.38, 128.11, 127.73, 127.48, 127.06, 126.81, 126.68, 126.61, 126.40, 126.06, 125.87, 125.59 (12t), 124.21, 123.90, 123.07, 122.97 (4q), 115.99, 115.81, 115.67, 115.54 (4t), 80.51, 80.39, 80.14, 80.04 (4q), 55.91, 54.46, 50.77, 49.48 (4t), 45.76, 44.52, 39.35, 38.98, 38.13, 37.70, 33.43, 33.30, 32.18, 31.96, 31.43, 30.33, 28.94, 28.53 (14s), 28.36, 28.34 (2p), 24.46, 23.72 (2s), 20.38, 19.92 (2p).

Compound 5—3-(Boc-Dmt-Tic-NH-propyl)-6-(Boc-Dmt-Tic-NH-butyl)-2(1H)-pyrazinone (5)

Starting from 3-[Z—NH—(CH$_2$)$_3$]-6-[Z—NH—(CH$_2$)$_4$]-2(1H)-pyrazinone (126.5 mg, 0.25 mmol), the crude compound was purified with silica gel chromatography (2.8 cm×36 cm; CHCl$_3$:MeOH=20:1). Yield 203 mg (73%); mp 164-166° C.; R$_{f3}$=0.56; [α]$_D^{25}$ −8.12° (c=0.36, MeOH). Anal. Calcd for C$_{64}$H$_{82}$N$_8$O$_{11}$·2H$_2$O: C, 65.3; H, 7.32; N, 9.53. Found: C, 65.3; H, 7.17; N, 9.54. $^1$H NMR (400 MHz, CDCl$_3$): 7.75-7.43 (m, 1H), 7.25-6.72 (m, 8H), 6.72-6.4 (m, 4H), 5.68-5.40 (m, 1.75H), 5.30 4.97 (m, 3.15H), 4.85-4.33 (m, 3.52H), 4.02-3.73 (m, 1.8H), 3.64-2.88 (m, 10.56H), 2.88-2.05 (m, 20.9H), 2.05-1.53 (m, 1.67H), 1.53-0.52 (m, 23.68H). $^{13}$C NMR (CDCl$_3$): 173.63, 173.36, 171.15, 170.52, 169.71, 169.44, 156.76, 156.39, 156.06, 155.84, 155.55, 155.32, 155.18, 155.10, 138.99, 138.89, 138.80, 138.55, 133.80, 133.54, 133.50, 133.27, 131.66, 131.44, 131.06, 130.92 (26q), 128.54, 128.30, 127.99, 127.50, 127.07, 126.71, 126.64, 126.17, 125.91, 125.62 (10t), 124.24, 123.99, 123.55, 122.96 (4q), 116.14, 116.05, 115.78, 115.53 (4t), 8.057, 80.45, 80.12, 80.04 (4q), 55.96, 53.80, 50.84, 49.36 (4t), 45.61, 44.68, 38.83, 38.00, 37.21, 33.46, 32.12, 31.52, 30.85, 30.49, 28.96, 28.79 (12s), 28.36, 28.35 (2p), 28.05, 27.04, 24.07, 23.84 (4s), 20.39, 19.99, 19.92, 17.84 (4p).

Compound 6—3-(Boc-Dmt-Tic-NH-butyl)-6-(Boc-Dmt-Tic-NH-propyl)-2(1H)-pyrazinone (6)

Starting from 3-[Z—NH—(CH$_2$)$_4$]-6-[Z—NH—(CH$_2$)$_3$]-2(1H)-pyrazinone (136 mg, 0.27 mmol), the crude compound was purified with silica gel chromatography (2.6 cm×34 cm); AcOEt:MeOH=20:1). Yield 145 mg (47.2%); mp 164-165° C.; R$_{f2}$=0.57; [α]$_D^{25}$ −4.0° (c-0.33, MeOH). Anal. Calcd for C$_{64}$H$_{82}$N$_8$O$_{11}$ 0.87H$_2$O: C, 66.4; H, 7.26; N, 9.68. Found: C, 66.5; H, 7.15; N, 9.68. $^1$H NMR (400 MHz, CDCl$_3$): 8.8 (br, 1H), 8.0-7.3 (m, 1H), 7.2-6.7 (m, 8H), 6.7-6.4 (m, 4H), 5.6-5.3 (m, 1.85H), 5.3-4.85 (m, 3H), 4.85-4.25 (m, 3.17H), 4.0-3.7 (m, 1.6H), 3.45-2.72 (m, 10.53H), 2.70-1.77 (m, 21.35H), 1.6-0.8 (m, 25H). $^{13}$C NMR (CDCl$_3$): 173.92, 173.28, 171.13, 170.96, 170.06, 169.91, 156.55, 156.33, 156.23, 155.90, 155.82, 177.71, 155.49, 155.26, 155.15, 138.99, 138.75, 138.64, 133.69, 133.66, 133.48, 133.02, 131.63, 131.28 (24q), 128.41, 128.35, 128.23, 127.71, 127.40, 126.94, 126.82, 126.38, 126.23, 125.90 (10t), 124.09, 122.94 (2q), 115.86, 115.70 (2t), 80.70, 80.39, 80.19, 80.05 (4q), 55.93, 54.54, 54.13, 50.85, 50.43, 49.50 (6t), 45.75, 44.66, 44.10, 38.96, 38.20, 37.93, 33.50, 32.00, 31.45, 30.57, 30.12, 28.70 (12s), 28.37, 28.32 (2p), 26.41, 25.55, 23.72, 23.58 (4s), 20.23, 20.35, 19.97, 17.90 (4p).

Compound 7—3-(Boc-Dmt-Tic-NH-ethyl)-6-(Boc-Dmt-Tic-NH-butyl)-2(1H)-pyrazinone (7)

Starting from 3-[Z—NH—(CH$_2$)$_2$]-6-[Z—NH—(CH$_2$)$_4$]-2(1H)-pyrazinone (130 mg, 0.264 mmol), the crude compound was purified with silica gel chromatography (3.2 cm×30 cm; CHCl$_3$:MeOH=20:1). Yield 185 mg (62.3%); mp 172-174° C.; R$_{f3}$=0.57; [α]$_D$ −6.0° (c=0.36, MeOH). Anal. Calcd for C$_{63}$H$_{80}$N$_8$O$_{11}$ 1.7H$_2$O: C, 65.4; H, 7.21; N, 9.69. Found: C, 65.4; H, 7.08; N, 9.69. $^1$H NMR (400 MHz, CDCl$_3$): 7.9-7.36 (m, 0.5H), 713-6.4 (m, 12H), 5.66-5.4 (m, 1.7H), 5.26-4.97 (m, 3.3H), 4.77-4.20 (m, 3.3H), 3.94-3.60 (m, 2.5H), 3.50-2.58 (m, 11.4H), 2.5-1.8 (m, 19.8H), 1.5-0.67 (m, 22.5H). $^{13}$C NMR (CDCl$_3$): 173.95, 173.29, 171.16, 170.33, 170.06, 169.93, 157.07, 156.41, 155.93, 155.84, 155.70, 155.52, 155.20, 155.13, 152.13, 151.88, 138.98, 138.85, 138.76, 138.57, 133.79, 133.67, 133.64, 133.14, 131.61, 131.23, 131.17, 131.14 (28q), 128.43, 127.99, 127.81, 127.42, 127.07, 126.99, 126.95, 126.72, 126.65, 126.09, 125.88, 125.63 (12q), 124.30, 124.00, 122.98 (3q), 116.22, 116.07, 115.61, 115.50 (4t), 80.43, 80.25, 80.11, 80.05 (4q), 55.92, 54.59, 50.68, 49.36 (4t), 45.74, 44.52, 37.91, 37.36, 36.84, 33.33, 32.27, 31.70, 31.36, 30.41, 28.92 (11s), 28.37, 28.34 (2p), 28.17, 24.19 (2s), 20.37, 20.30, 20.03, 17.79 (4p).

Example 2

This example illustrates the general procedure for synthesis of compounds 8-14 described below. 3,6-Bis(Boc-Dmt-Tic-NH-alkyl)-2(1H)-pyrazinone (compounds 1-7, 0.12 mmol) were treated with TFA (0.8 mL, 10 mmol) and anisole (40 ml) for 1 hr at room temperature. The reaction solution was diluted with hexane, the solid was collected by filtration, dried over KOH pellets and purified by semi-preparative RP-HPLC. The purified peptide was lyophilized from water containing 1N HCl (0.25 mL) for three times to give amorphous powder.

In accordance with the procedure recited in this Example, compounds 8-14, listed below, were synthesized from compounds 1-7, respectively.

Compound 8—3,6-Bis(Dmt-Tic-NH-methyl)-2(1H)-pyrazinone 2HCl (8)

Yield 95 mg (83%); mp 224-226° C. (dec.); R$_{f5}$=0.15; R$_{f6}$=0.73; t$_R$=14.44 min; [α]$_D^{25}$ +27.02° (c=0.35, H$_2$O); m/z 870 (MH⁺). ¹H NMR (400 MHz, DMSO-$d_6$): 9.2 (br, 2H), 8.78 (s, 5H), 8.6-8.2 (m, 3.4H), 7.2-6.7 (m, 8.6H), 6.55-6.2 (m, 4H), 5.05-4.9 (m, 1H), 4.68-4.44 (m, 1.5H), 4.44-3.86 (m, 8.5H), 3.23-2.88 (m, 5H), 2.88-2.67 (m, 1.5H), 2.32-1.83 (m, 1.5H), 1.57-1.36 (m, 1.5H). ¹³C NMR (DMSO-$d_6$): 169.04, 168.98, 168.40, 168.05, 156.07, 155.87, 154.13, 138.48, 138.44, 138.41, 138.30, 132.00, 131.88, 131.45, 131.24 (15q), 127.87, 127.74, 126.44, 126.29, 126.09, 125.99, 125.86, 125.60 (8t), 121.34, 121.25, 121.04, 120.99 (4q), 115.07, 54.96, 54.89, 47.81, 47.69 (5t), 43.24, 42.70, 38.98, 31.06, 2330.38, 28.99, 28.37 (7s), 20.02, 19.98, 19.51, 17.94 (4p).

Compound 9—3,6-Bis(Dmt-Tic-NH-ethyl)-2(1H)-pyrazinone2HCl (9)

Yield 97 mg (77%); mp 226-228° C.; $R_{f5}$=0.16; $R_{f6}$=0.74; $t_R$=14.46 min; $[α]_D^{25}$ +10.04° (c=0.48, H20); m/z 898 (MH⁺). ¹H NMR (400 MHz, DMSO-$d_6$): 8.9-8.37 (m, 6H), 8.27 (br, 0.8H), 8.08 (br, 0.8H), 7.86 (br, 0.2H), 7.55 (br, 0.2H), 7.4-6.7 (m, 8H), 6.5-6.2 (m, 4H), 5.08-4.95 (m, 0.38H), 4.86-1.7 (m, 1.62H), 4.6-4.1 (m, 4H), 3.9-3.8 (m, 1.62H), 3.55-3.45 (m, 0.38H), 3.34-2.85 (m, 9.3H), 2.85-2.35 (m, 5H), 2.35-1.9 (m, 14.7H), 1.5-1.35 (m, 1.5H). ¹³C NMR (DMSO-$d_6$): 169.09, 169.06, 168.30, 168.13, 156.04, 138.47, 138.39, 132.06, 131.88, 131.40, 131.35 (11q), 127.76, 126.39, 126.05, 125.99, 125.92, 125.43 (6t), 121.39, 121.06, 120.98 (3q), 115.06, 55.09, 54.99, 48.80, 47.83 (5t), 43.21, 43.07, 37.37, 31.09, 31.00, 29.15, 28.97 (8s), 20.02, 19.58, 19.54, 19.49, 17.18 (5p).

Compound 10—3,6-Bis(Dmt-Tic-NH-propyl)-2(1H)-pyrazinone-2HCl (10)

Yield 81 mg (74.3%), mp 222-223° C.; $R_{f5}$=0.16; $R_{f6}$=0.75; $t_R$=14.89 min; $[α]_D^{25}$ +22.07° (c=0.42, H₂O); m/z 926 (MH⁺). ¹H NMR (400 MHz, DMSO-$d_6$): 8.9-8.4 (m, 6H), 8.24 (br, 0.8H), 8.11 (br, 0.8H), 7.49 (br, 0.4H), 7.2-6.8 (m, 8H), 6.5-6.25 (m, 4H), 5.05-4.95 (m, 0.4H), 4.82-4.66 (m, 1.6H), 4.57-4.1 (m, 4H), 3.92-4.76 (m, 1.6H), 3.6-3.5 (2dd, 0.4H, J=4.20 Hz), 3.25-2.65 (m, 10.85H), 2.58-1.85 (m, 18.65H), 1.67-1.27 (m, 5.5H). ¹³C NMR (DMSO-$d_6$): 169.10, 169.01, 168.09, 167.97, 156.08, 156.04, 155.98, 155.57, 138.46, 138.38, 132.14, 132.10, 131.63, 131.48 (14q), 127.75, 127.67, 126.43, 126.08, 126.04, 125.99, 125.4 (7t), 121.39, 121.03, 121.02 (3q), 115.10, 55.03, 54.99, 52.70, 52.50, 48.70, 48.01, 47.93 (8t), 44.62, 43.41, 43.26, 38.47, 38.28, 31.06, 30.36, 29.46, 29.35, 28.43, 27.60, 26.74, 26.12 (13s), 20.02, 19.51, 19.49, 17.26 (4p).

Compound 11—3,6-Bis(Dmt-Tic-NH-butyl)-2(1H)-pyrazinone 2HCl (11)

Yield 98 mg (84.8%); mp 219-220° C.; $R_{f5}$=0.14; $R_{f6}$=0.74; $t_R$=14.74 min; $[α]_D^{25}$ +22.54° (c=0.42, H₂O); m/z 954 (MH⁺). ¹H NMR (400 MHz, DMSO-$d_6$): 8.98-8.40 (m, 6H), 8.14 (s, 0.8H), 8.04 (s, 0.85H), 7.23-6.7 (m, 8.35H), 6.50-6.25 (m, 4H), 5.01 (t, 0.4H), J=4.56 Hz), 4.75-4.64 (m, 1.6H), 475-4.64 (m, 0.8H), 4.57-4.4 (m, 0.8H), 4.38-4.24 (m, 1.6H), 3.85-3.75 (m, 1.6H), 3.54 (d, 0.4H, J=15.01 Hz), 3.26-2.85 (m, 9.2H), 2.78 (d, 1.6H, J=15.97 Hz), 2.6-2.45 (m, 1.2H), 2.43-1.95 (m, 17II), 1.7-0.9 (m, 10H). ¹³C NMR (DMSO-$d_6$): 169.10, 169.07, 168.98, 168.94, 167.85, 167.83, 156.09, 156.06, 155.98, 155.66, 138.43, 138.36, 138.43, 132.56, 132.37, 132.21, 132.15, 131.66, 131.53 (19q), 127.68, 126.66, 126.40, 126.35, 126.17, 126.08, 126.03, 125.98, 125.95, 125.45 (10t), 121.36, 121.03 (2q), 115.11, 55.02, 52.70, 48.62, 48.07 (5t), 44.71, 43.57, 43.52, 38.41, 38.06, 31.00, 30.76, 29.66, 29.40, 28.77, 28.55, 28.30, 24.95, 23.55 (14s), 19.98, 19.50, 19.47, 17.06 (4p).

Compound 12—3-(Dmt-Tic-NH-propyl)-6-(Dmt-Tic-NH-butyl)-2(1H)-pyrazinone-2HCl (12)

Yield 105 mg (91.3%); mp 222-224° C.; $R_{f5}$=0.17; $R_{f6}$=0.74; $t_R$=15.01 min; $[α]_D^{25}$ +24.05° (c=0.36, H₂O); m/z 940 (MH⁺). ¹H NMR (400 MHz, DMSO-$d_6$): 8.9-8.35 (m, 6H), 8.2-8.0 (m, 1.6H), 7.50 (br, 0.2H), 7.2-6.75 (m, 8.2H), 6.52-6.25 (m, 4H), 4.96-4.87 (m, 0.4H), 4.72 (t 1.6H, J=16.70 Hz), 4.58-4.10 (m, 4H), 3.87-3.73 (m, 1.6H), 3.55 (dd, 0.4H, J=7.73, 15.32 Hz), 3.38-2.84 (m, 9.2H), 2.79 (d, 1.65H, J=13.90 Hz), 2.6-1.9 (m, 18.65H), 1.58-1.47 (m, 3.5H), 1.37-0.94 (m, 4H). ¹³C NMR (DMSO-$d_6$): 169.11, 169.08, 169.04, 168.97, 167.98, 167.83, 156.09, 156.04, 155.94, 155.59, 138.43, 138.36, 132.55, 132.49, 132.47, 132.28, 132.20, 132.11, 131.63, 131.53 (20q), 127.68, 126.43, 126.35, 126.04, 125.98, 125.95, 125.44 (7t), 121.39, 121.35, 121.03, 121.02 (4q), 115.11, 55.00, 52.53, 48.65, 48.02 (5t), 4.72, 43.52, 43.41, 38.51, 38.22, 38.05, 37.67, 31.04, 30.98, 29.55, 29.44, 28.74, 28.55, 28.30, 26.18, 24.97 (16s), 20.03, 19.98, 19.50, 19.49, 17.04, 17.31 (6p).

Compound 13—3-(Dmt-Tic-NH-butyl)-6-(Dmt-Tic-NH-propyl)-2(1H)-pyrazinone2HCl (13)

Yield 78 mg (87.8%); mp 224-226° C.; $R_{f5}$=0.15; $R_{f6}$=0.73; $t_R$=14.78 min; $[α]_D^{25}$ +28.10°(c=0.41, H₂O); m/z 940 (MH⁺). ¹H NMR (400 MHz, DMSO-$d_6$): 9.0-8.3 (m, 6H), 8.25 (br, 0.76H), 8.03 (br, 0.76H), 7.56-6.07 (m, 8.5H), 7.6-6.1 (m, 4H), 5.05-4.95 (m, 0.4H), 4.85-4.6 (m, 1.6H), 4.6-4.1 (m, 4H), 3.97-3.7 (m, 1.6H), 3.6-3.5 (m, 0.4H), 3.1-2.67 (m, 10.5H), 2.4-1.8 (m, 17.3H), 1.7-1.1 (m, 9.2H). ¹³C NMR (DMSO-$d_6$): 169.29, 169.22, 169.10, 168.93, 168.09, 167.84, 165.08, 156.03, 155.97, 155.65, 138.45, 138.43, 138.39, 138.35, 132.15, 131.65, 131.48 (17q), 127.76, 127.65, 126.43, 126.39, 126.08, 126.02, 125.44 (7t), 121.37, 121.03 (2q), 115.10, 55.03, 52.61, 48.71, 48.62, 48.07, 47.92 (7t), 44.70, 43.58, 43.35, 38.38, 38.27, 37.78, 31.03, 30.68, 29.66, 29.34, 28.53, 27.59, 26.83, 23.52 (14s), 20.02, 19.98, 19.51, 19.47, 17.0 (5s).

Compound 14—3-(Dmt-Tic-NH-ethyl)-6-(Dmt-Tic-NH-butyl)-2(1H)-pyrazinone 2HCl (14)

Yield 106 mg (98%); mp 225-227° C.; $R_{f5}$=0.16; $R_{f6}$=0.74; $t_R$=14.59 min; $[α]_D^{25}$ +17.66° (c=0.40, H₂O); m/z 926 (MH+). ¹H NMR (400 MHz, DMSO-$d_6$): 8.9-8.36 (m, 6H), 8.28-7.93 (m, 1.65H), 7.17-6.74 (m, 8.32H), 6.5-6.18 (m, 4H), 5.06-4.96 (m, 0.36H), 4.87-4.63 (m, 1.64H), 4.56-4.10 (m, 4H), 3.90-3.75 (m, 1.64H), 3.58-3.47 (m, 0.36), 3.33-2.54 (m, 13.2H), 2.47-1.93 (m, 15.8H), 1.63-1.0 (m, 6H). ¹³C NMR (DMSO-$d_6$): 169.11, 169.09, 169.05, 168.99, 168.20, 167.86, 156.12, 156.07, 156.05, 155.99, 138.48, 138.36, 132.16, 132.02, 131.55, 131.32 (16q), 127.78, 127.68, 126.70, 126.39, 126.07, 125.99, 125.94, 125.45 (8t), 121.41, 121.36, 121.09, 121.02 (4q), 115.11, 115.05, 55.09, 55.02, 52.69, 52.51, 48.75, 48.64, 48.02, 47.83 (10t), 44.71, 44.54, 43.52, 43.05, 38.11, 37.56, 31.21, 30.99, 30.33, 29.56, 28.92, 28.55, 28.25, 25.07 (14s), 20.02, 19.98, 19.57, 19.50, 17.65, 16.89 (6t).

Example 3

This example illustrates the general procedure for synthesis of compounds 15-17 described below. To a solution of diaminoalkane (0.259 mmol) in DMF (10 mL), Boc-Dmt-Tic-OH (0.534 mmol), DIPEA (112 mL, 0.64 mmol), and PyBop (0.292 g, 0.56 mmol) were added. The reaction mixture was stirred at 0° C. for 10 min, then room temperature for 4 hours. After removal of solvent, the residue was diluted with AcOEt. The organic phase was washed with ice cold 10% citric acid (3×10 mL), 5% $Na_2CO_3$ (3×10 mL) and saturated aqueous NaCl (3×10 mL), dried over $Na_2SO_4$ and evaporated to dryness. The residue was purified by flash chromatography. The compound was precipitated with hexane, filtered and dried in vacuo.

Compound 15—1,4-Bis(Boc-Dmt-Tic-amino)butane (15)

Starting from 1,4-diaminobutane (22.8 mg, 0.259 mmol), the crude compound was purified by silica gel chromatography (3.2 cm×33 cm; AcOEt:hexane=4:1). Yield 145 mg (56.6%); mp 154-155° C.; $R_{f1}$=0.27; $[\alpha]_D^{25}$ −8.08° (c=0.27, MeOH). Anal. Calcd for $C_{56}H_{72}N_6O_{11}$ $8H_2O$: C, 67.1; H, 7.34; N, 8.38. Found: C, 66.9; H, 7.29; N, 8.45. $^1H$ NMR (400 MHz, $CDCl_3$): 7.4-7.2 (m, 1H), 7.2-6.7 (m, 8.35H), 6.6-6.4 (m, 4H), 5.6-5.3 (m, 2H), 5.3-4.83 (m, 3.5H), 4.8-4.55 (m, 2H), 4.55-4.3 (m, 1.71H), 4.0-3.85 (m, 0.94H), 3.75 (t, 0.98H, J=16.0 Hz), 3.5-2.65 (m, 10.6H), 2.65-1.95 (m, 13.74H), 1.95-1.72 (m, 0.74H), 1.6-1.3 (m, 18H), 1.1-0.5 (m, 4H). $^{13}C$ NMR ($CDCl_3$): 173.92, 173.90, 173.88, 173.12, 170.63, 170.28, 170.03, 155.98, 155.69, 155.62, 155.36, 155.09, 138.82, 133.64, 133.44, 132.80, 131.54, 131.41, 131.20 (19q), 128.38, 128.30, 128.17, 127.75, 127.61, 127.24, 127.14, 126.91, 126.80, 126.68, 126.15, 125.77 (12t). 123.96, 123.78, 123.40 (3q), 115.66, 115.57, 115.51, 115.47 (4t), 80.71, 80.14, 80.07 (3q), 55.87, 54.46, 54.27, 50.34, 49.63, 49.38 (6t), 45.65, 44.05, 39.26, 38.80, 38.57, 33.51, 33.37, 32.44, 31.59, 31.42, 31.33, 30.03 (12s), 28.37, 28.33, 28.30 (3p), 26.27, 25.76, 25.44, 22.65 (4s), 2.83, 20.34, 19.96 (3p).

Compound 16—1,6-Bis(Boc-Dmt-Tic-amino)hexane (16)

Starting from 1,6-diaminohexane (30.1 mg, 0.259 mmol), the crude compound was purified by silica gel chromatography (3.2 cm×37 cm; AcOEt:hexane=3:1). Yield 170 mg (64.6%); mp 159-160° C.; $R_{f1}$=0.48; $[\alpha]D25$+0.03° (c=0.30, MeOH). Anal. Calcd for $C_{58}H_{76}N_6O_{11}$ $3.5H_2O$: C, 64.43; H, 7.68; N, 7.77. Found: C, 64.39; H, 7.24; N, 7.80. $^1H$ NMR (400 MHz, DMSO-$d_6$): 9.3-8.2 (br, 1.5H), 7.9-7.6 (m, 1.2H), 7.4-6.7 (m, 10.4H), 6.5-6.1 (m, 4H), 4.9-4.3 (m, 4.7H), 4.3-4.0 (m, 3H), 3.2-2.7 (m, 11.32H), 2.3-1.8 (m, 12.8H), 1.8-0.7 (m, 26H). $^{13}C$ NMR (DMSO-$d_6$): 172.0, 171.2, 169.82, 168.24, 168.21, 155.54, 155.39, 155.04, 154.65, 138.34, 138.01, 137.91, 133.68, 133.57, 132.70, 131.79 (16q), 127.76, 127.60, 126.83, 126.25, 126.16, 125.96, 125.87, 125.84, 125.31 (9t), 124.44, 122.94 (2q), 114.89, 114.65 (2t), 78.60, 78.56, 77.88 (3q), 54.85, 53.28, 50.18, 49.47 (4t), 44.71, 42.86, 38.69, 38.18, 35.68, 31.62, 31.18, 30.85, 29.18, 28.93, 28.51, 28.43 (12s), 28.04, 27.94, 27.62, 27.45 (4p), 25.75, 25.66, 25.60 (3s), 20.16, 19.45 (2p).

Compound 17—1,10-Dis(Boc-Dmt-Tic-amino)decane (17)

Starting from 1,10-diaminodecane (53.5 mg, 0.311 mmol), the crude compound was purified by silica gel chromatography (3.2 cm×35 cm; AcOEt:hexane=3:1). Yield 208 mg (62.4%); mp 145-147° C.; $R_{f1}$=0.54; $[\alpha]_D^{25}$ −2.14° (c=0.44, MeOH). Anal. Calcd for $C_{62}H_{84}N_6O_{10}$·$4H_2O$: C, 64.95; H. 8.03; N, 7.33. Found: C, 64.63; H, 7.70; N, 7.29. $^1H$ NMR (400 MHz, DMSO-$d_6$): 8.98 (br, 2H), 7.9-7.6 (m, 1.5H), 7.3-6.75 (m, 10.3H), 6.5-6.3 (m, 4H), 5.0-3.9 (m, 7.5H), 3.7-3.5 (m, 0.5H), 3.1-2.7 (m, 11.5H), 2.3-2.0 (m, 12.5H), 1.73-1.58 (m, 1.3H), 1.43-0.8 (m, 22.7H). 13C NMR (DMSO-$d_6$): 172.01, 169.83, 169.28, 168.21, 167.93, 156.03, 155.53, 155.40, 155.03, 154.64, 138.33, 138.00, 132.71, 131.79 (14q), 127.77, 126.79, 126.22, 125.94, 125.77, 125.30 (6t), 124.41, 122.92 (2q), 114.88, 114.64 (2t), 78.54, 77.87 (2q), 54.82, 53.27, 50.16, 49.47 (4t), 44.65, 42.83, 38.40, 38.27, 31.58, 30.87, 29.11, 28.99, 28.80, 28.73, 28.54, 28.48 (12s), 28.04, 27.94 (2p), 26.01 (s), 20.15, 19.44 (2p).

Example 4

This example illustrates the general procedure for synthesis of compounds 18-20 described below. Bis(Boc-Dint-Tic-amino)-alkane (compounds 15-17, 0.167 mmol) was treated with TFA (1.0 mL, 13 mmol) and anisole (50 ml) for 1 hr at room temperature. The reaction solution was diluted with hexane and the solid was collected by filtration, dried over KOH pellets and purified by semi-preparative RP-HPLC. The purified peptide was lyophilized from water containing 1N HCl (0.25 mL) for three times to give an amorphous powder.

In accordance with the procedure recited in this Example, compounds 18-22, listed below, were synthesized from compounds 15-17, respectively.

Compound 18—1,4-Bis(Dmt-Tic-amino)butane-2HCl (18)

Yield 137 mg (95.2%); mp 215-217° C.; $R_{f5}$=0.19; $R_{f6}$=0.74; $t_R$=14.50 min; $[\alpha]_D^{25}$ +23.55° (c=0.41, $H_2O$); m/z 790 ($MH^+$). $^1H$ NMR (400 MHz, DMSO-$d_6$): 9.27 (br, 2H), 8.95-8.3 (m, 6H), 8.04-7.73 (m, 1.4H), 7.2-6.7 (m, 8.6H), 6.5-6.25 (m, 4H), 5.02-4.92 (m, 0.4H), 4.75-4.6 (m, 1.6H), 4.55-4.13 (m, 4H), 3.8-3.7 (m, 1.6H), 3.57-3.48 (m, 0.4H), 3.2-2.65 (m, 10.5H), 2.3-1.8 (m, 12H), 1.65-1.53 (m, 1.5H), 1.05-0.6 (m, 4H). $^{13}C$ NMR (DMSO-$d_6$): 169.18, 169.09, 169.07, 168.92, 167.81, 167.78, 156.05, 155.97, 138.42, 138.34, 132.57, 132.39, 132.24, 132.20, 131.65 (15q), 127.66, 126.73, 126.46, 126.12, 125.97, 125.41 (6t), 121.36, 120.98 (2q), 115.09, 54.99, 52.65, 48.67, 48.06 (5t), 44.66, 43.58, 38.18, 37.81, 31.27, 30.97, 30.34, 29.65, 25.85, 25.78 (10s), 19.98, 19.57 (2p).

Compound 19—1,6-Bis(Dmt-Tic-amino)hexane-2HCl (19)

Yield 100 mg (93.6%); mp 215-217° C.; $R_{f5}$=0.22; $R_{f6}$=0.74; $t_R$=15.01 min; $[\alpha]_D^{25}$ +32.3° (c=0.41, $H_2O$); m/z 818 ($MH^+$). $^1H$ NMR (400 MHz, DMSO-$d_6$): 9.28 (s, 2H), 8.9-8.3 (m, 6H), 8.02-7.9 (m, 1.5H), 7.2-6.75 (m, 8.5H), 6.55-6.3 (m, 4H), 5.05-4.98 (m, 0.41H), 4.74-4.6 (m, 1.55H), 4.58-4.4 (m, 0.88H), 4.38-4.25 (m, 1.57H), 4.2-4.05 (m, 1.52H), 3.82-3.7 (m, 1.57H), 3 58-3.5 (m, 0.41H), 3.2-2.9 (m, 10.5H), 2.4-1.9 (m, 12H), 1.67-1.56 (m, 1.5H), 1.1-0.7 (m, 8H). 13C NMR (DMSO-$d_6$): 169.32, 169.11, 168.84, 167.68, 156.08, 156.01, 1388.42, 138.35, 132.50, 132.21, 132.15, 132.10, 131.55 (13q), 127.74, 127.64, 126.75, 126.47, 126.23, 126.19, 125.98, 125.45 (8t), 121.33, 121.00 (2q), 115.10, 55.01, 52.59, 48.58, 48.05 (5t), 44.67, 43.63, 38.49, 38.13, 31.24, 31.00, 30.36, 29.62, 28.85, 28.65, 25.61, 25.53 (12s), 19.96, 19.47 (2p).

Compound 20—1,10-Bis(Drat-Tic-amino)decane-2HCl (20)

Yield 108 mg (81.6%); mp 205-207° C.; $R_{f5}$=0.32; $R_{f6}$=0.75; $t_R$=17.22 min; $[\alpha]_D^{25}$ +5.36° (c=0.55, $H_2O$); m/z 874 (MH+). $^1$H NMR (400 MHz, DMSO-d$_6$): 9.25 (br, 2H), 8.9-8.3 (m, 6H), 8.00 (t, 1.6H, J=5.74 Hz), 7.2-6.75 (m, 8.4H), 6.5-6.3 (m, 4H), 5.05-5.0 (m, 0.4H), 4.72-4.64 (m, 1.6H), 4.56-4.42 (m, 0.8H), 4.36-4.28 (m, 1.6H), 4.2-4.1 (m, 1.6H), 3.56-3.52 (m, 0.4H), 3.2-2.7 (m, 10.5H), 2.3-1.9 (m, 12H), 1.60 (dd, 1.5H, J=5.2, 15.6 Hz), 1.2-0.8 (m, 16H). $^{13}$C NMR (DMSO-d$_6$): 169.38, 169.12, 168.85, 167.69, 156.09, 156.04, 138.41, 138.34, 132.56, 132.22, 132.17, 131.59 (12q), 127.74, 127.66, 126.69, 126.42, 126.20, 126.12, 125.98, 125.48 (8t), 121.34, 121.02 (2q), 115.11, 55.02, 52.61, 48.56, 48.05 (5t), 44.71, 43.60, 38.56, 38.20, 31.22, 31.01, 30.36, 29.63, 28.96, 28.79, 28.76, 28.67, 28.61, 28.58, 25.90 (15s), 19.96, 19.48 (2p).

Compound 21—1,6-Bis(N,N-Dimethyl-Dmt-Tic-NH)-hexane 2HCl (21)

To a stirred solution of 1,6-bis(Dmt-Tic-amino)hexane-2TFA (19, 104.5 mg, 0.1 mmol) in 37% aqueous formaldehyde (0.149 mL, 2 mmol) in H$_2$O (4.5 mL) and acetonitrile (4.5 mL) was added sodium cyanoborohydride (37.7 mg, 0.6 mmol). Glacial acetic acid (0.02 mL) was added over 10 min and stirring was continued for 15 min. The solution was adjusted to pH 5 with TFA, evaporated, lyophilized, and the residue purified with RP-HPLC. Yield 67 mg (70.8%); mp 195-197° C.; R$_{f5}$=0.10; t$_R$=15.0 min, $[\alpha]_D^{25}$ −12.73° (c=0.44, H$_2$O); m/z 874 (MH+). $^1$H NMR (MeOD-d$_3$): 7.2-6.85 (m, 8H), 6.6-6.3 (m, 4H), 5.12-5.70 (m, 0.36H), 4.83-4.78 (m, 0.36H), 4.74-4.67 (m, 0.36H), 4.63-4.48 (m, 3.28H), 4.30 (dd, 1.64H, J=4.0, 12.04 Hz), 3.9-3.83 (m, 1.64H), 3.73-3.65 (m, 0.36H), 3.5-3.2 (m, 4H), 3.20-3.74 (m, 18H), 2.72-2.62 (m, 0.36H), 2.6-2.0 (m, 12H), 197-1.83 (m, 1.64H), 1.13-0.8 (m, 2H), 0.8-0.6 (m, 2H). $^{13}$C NMR (MeOD-d$_3$): 171.45, 170.65, 170.02, 169.74, 158.14, 157.96, 140.52, 140.44, 134.25, 132.96, 132.86, 132.68 (12q), 129.20, 128.93, 128.36, 128.30, 128.24, 128.20, 127.46, 127.00 (8t), 121.69, 121.65 (2q), 116.89, 116.79, 65.44, 65.00, 57.39, 56.25 (6t), 46.80, 45.97 (2s), 44.37, 43.52, 41.57 (3p), 40.52, 40.10, 32.75, 31.78, 30.06, 29.43, 27.03, 26.85 (8s), 20.70, 20.03 (2p).

Compound 22—3,6-Bis(N,N-dimethyl-Dmt-Tic-NH-propyl)-2(1H)-pyrazinone 2HCl (22)

3,6-Bis[Z—NH—(CH$_2$)$_3$]-2(1H)-pyrazinone (57.8 mg, 0.117 mmol) was stirred in 25% HBr/AcOH (0.42 mL, 1.76 mmol) with an ice bath for 10 min then room temperature for 3 hr. The resulting amine was precipitated with ether and dried in vacuo. The precipitate was dissolved in DMF (10 mL) containing DIPEA (147 ml, 0.846 mmol), to which N,N-dimethyl-Dmt-Tic-OH-TFA (120 mg, 0.235 mmol) and PyBop (128 mg, 0.247 mmol) were added. The solution was first stirred in an ice bath for 10 min, then room temperature for 4 h. After removal of the solvent in vacuu, the residue was diluted with AcOEt (60 mL), and the produced precipitate was collected by filtration, dried, and purified with RP-HPLC. Yield 58 mg (45.5%); mp 214-216° C.; R$_{f5}$=0.09; R$_{f6}$=0.59; t$_R$=14.7 min; $[\alpha]_D^{25}$ +0.92° (c=0.38, H$_2$O); m/z 982 (MH+). $^1$H NMR (DMSO-d$_6$): 10.85-10.04 (m, 1.67H), 8.3-8.0 (m, 1.72H), 7.25-6.75 (m, 8.4H), 6.65-6.1 (m, 4H), 4.8-4.4 (m, 5.76H), 4.2-3.96 (m, 1.76H), 3.5-2.66 (m, 23.48H), 2.66-1.65 (m, 18H), 1.65-1.2 (m, 6H). $^{13}$C NMR (DMSO-d$_6$): 169.20, 168.21, 168.14, 168.12, 168.00, 167.90, 156.11, 155.99, 138.54, 138.34, 131.59, 131.55, 131.27, 131.22 (14q), 127.63, 126.41, 126.27, 126.11 (4t), 120.27, 120.20 (2q), 115.12, 114.90, 61.80, 61.72, 55.36, 54.41 (6t), 45.00, 44.07 (2s), 41.78, 41.55, 40.41, 40.20 (4p), 38.46, 38.27, 29.80, 29.61, 28.42, 28.28, 27.43, 26.61, 26.10, 25.80 (10s), 20.01, 19.68, 17.25, 16.82 (4p).

Example 5

This example illustrates the general procedure for synthesis of compounds 23a and 24a—N,N-(Allyl)$_2$-Tyr-OMe (23a) and N-Allyl-Tyr-OMe (24a):

HCl Tyr-OMe (2.0 g, 8.6 mmol) was dissolved in methanol (20 ml), and DIPEA (4.8 mL, 27.5 mmol) and allylbromide (1.86 mL, 21.5 mmol) were added in sequence. After stirred in room temperature for 20 min, the temperature was raised to 50° C. and keep at this temperature for 5 hr. The mixture was evaporated to remove the solvent, the residue was dissolved in water (30 mL) and extracted with AcOEt (3×30 mL). The combined extracts were washed with saturated NaCl, dried over Na$_2$SO$_4$, filtered, and concentrated under reduced pressure. The residue was purified by flash chromatography (SiO$_2$, AcOEt:hexane=1:1) to give pure N,N-(allyl)$_2$-Tyr-OMe (23a) (1.34 g, 59.3%) and N-allyl-Tyr-OMe (24a) (0.74 g, 36.4%). N,N-(allyl)$_2$-Tyr-OMe (23a): mp 127-128° C., R$_f$=0.79 (AcOEt:hexane=1:1), $[\alpha]_D^{25}$ −198° (c=0.63, MeOH). $^1$H NMR (400 MHz, CDCl$_3$) δ: 7.04 (d, 2H, J=8.32 Hz), 6.73 (d, 2H, J=8.32 Hz), 5.77-5.58 (m, 2H), 5.20-5.0 (m, 4H), 4.68 (br, 1H), 3.7-3.55 (m, 4H), 3.44-3.30 (m, 2H), 3.17-2.93 (m, 3H), 2.90-2.75 (m, 1H). N-Allyl-Tyr-OMe (24a): mp 117-118° C., R$_f$=0.74 (AcOEt), $[\alpha]_D^{25}$ +27° (c=0.51, MeOH). $^1$H NMR (400 MHz, CDCl$_3$) δ: 7.02 (d, 2H, J=8.56 Hz), 6.71 (d, 2H, J=8.56 Hz), 5.88-5.76 (m, 1H), 5.18-5.07 (m, 2H), 3.67 (s, 3H), 3.57 (t, 1H, J=6.6 Hz), 3.34-3.27 (m, 1H), 3.20-3.12 (m, 1H), 2.94 (d, 2H, J=6.6 Hz).

Example 6

This example illustrates the general procedure for synthesis of compound 23b and 24b—N,N-Diallyl-Dmt-OMe (23b) and N-allyl-Dmt-OMe (24b):

HCl Dmt-OMe (3.0 g, 11.55 mmol) was dissolved in MeOH (60 ml), and DIPEA (6 mL, 34.65 mmol) and allylbromide (2 mL, 23.1 mmol) were added in sequence. After stirred in room temperature for 20 min, the temperature was raised to 50° C. and kept at this temperature for 5 hr. The mixture was evaporated to remove the solvent, the residue was dissolved in water (50 mL) and extracted with AcOEt (3×50 mL). The combined extracts were washed with saturated NaCl, dried over Na$_2$SO$_4$, filtered, and concentrated under reduced pressure. The residue was purified by flash chromatography (SiO$_2$, AcOEt:hexane=1:1) to give pure N,N-(allyl)$_2$-Tyr-OMe (23b) 1.05 g (30%) and N-allyl-Dmt-OMe (24b) 1.72 g (56.7%). N,N-(allyl)$_2$-Tyr-OMe (23b): oil, R$_f$=0.76 (AcOEt:hexane=1:1); $[\alpha]_D^{25}$ 2.54° (c=0.55, MeOH). $^1$H NMR (400 MHz, DMSO-d$_6$) δ: 8.93 (s, 1H), 6.37 (s, 2H), 5.74-5.63 (m, 2H), 5.20-5.04 (m, 4H), 3.50 (s, 3H), 3.46 (dd, 1H, J=5.41, 8.74 Hz), 3.43-3.93 (m, 1H), 3.39-3.36 (m, 1H), 3.04-2.95 (m, 3H), 2.70 (dd, 1H, J=5.40, 14.12 Hz), 2.16 (s, 6H). N-Allyl-Dmt-OMe (24b): oil, R$_f$=0.53 (AcOEt: hexane=1:1); $[\alpha]_D^{25}$ 42.12° (c=0.34, MeOH). $^1$H NMR (400 MHz, DMSO-d$_6$) δ: 8.93 (s, 1H), 6.38 (s, 2H), 5.78-5.60 (m, 1H), 5.08-4.95 (m, 2H), 3.53 (m, 3H), 3.29 (t, 1H, J=9.28 Hz), 3.17-3.08 (m, 1H), 2.98-2.90 (m, 1H), 2.83-2.70 (m, 2H), 2.16 (s, 6H).

Example 7

This example illustrates the general procedure for synthesis of compound 25a—N,N-(Allyl)$_2$-Tyr-OH (25a):

With a ice bath, 1 N NaOH (11 mL, 11 mmol) was added to a solution of N,N-(allyl)-2-Tyr-OMe (23a) (1.31 g, 4.8 mmol) in methanol (15 mL), the resulting solution was stirred at room temperature for over night. The solvent was removed in vacuo, the pH of the residue was adjusted to 3, the resulted precipitate was filtered, washed with cold water, and dried under vacuo. Yield 0.866 g (69%), mp 214-216° C. (ref. 196-198° C.), $R_f$=0.43 (n-BnOH:H$_2$O:HOAc=4:1:5), $[\alpha]_D^{25}$ −6.1 (c=0.72, MeOH). $^1$H NMR (400 MHz, DMSO-d$_6$) δ: 12.2 (br, 1H), 9.2 (br, 1H), 6.95 (d, 2H, J=8.4 Hz), 6.63 (d, 2H, J=8.4 Hz), 5.73-5.56 (m, 2H), 5.11 (d, 2H, J=17.24 Hz), 5.04 (d, 2H, J=10.24 Hz), 3.43 (t, 1H, J=7.54 Hz), 3.28 (dd, 2H, J=5.05, 14.8 Hz), 3.06 (dd, 2H, J=6.92, 14.80 Hz), 2.82 (dd, 1H, J=7.82, 13.65 Hz), 2.67 (dd, 1H, J=7.31, 13.65).

Example 8

This example illustrates the general procedure for synthesis of compound 25b—N,N-Diallyl-Dmt-OH (25b):

With a ice bath, 1 N NaOH (8 mL, 8 mmol) was added to a solution of N,N-(allyl)-2-Dmt-OMe (23b) (0.967 g, 3.19 mmol) in methanol (10 mL), the resulting solution was stirred at room temperature for over night. The solvent was removed in vacuo, the pH of the residue was adjusted to 3, the resulted precipitate was extracted with AcOEt (3×50 mL), the combined extract was washed with saturated NaCl (2×50 mL), dried over Na$_2$SO$_4$, filtered, and purified by flash chromatography (SiO$_2$, AcOEt:MeOH=10:1). Yield 428 mg (46.5%), mp 205-207° C., $R_f$=0.5 (AcOEt:MeOH=10:1), $[\alpha]_D^{25}$ +25.2° (c=0.68, MeOH). $^1$H NMR (400 MHz, DMSO-d$_6$) δ: 12.2 (br, 1H), 8.89 (s, 1H), 6.37 (s, 1H), 5.74-5.62 (m, 2H), 5.13 (dd, 2H, J=1.29, 17.21 Hz), 5.05 (dd, 2H, J=1.0, 10.23 Hz), 3.42-3.34 (m, 3H), 3.06-2.90 (m, 3H), 2.66 (dd, 1H, J=5.70, 14.1 Hz).

Example 9

This example illustrates the general procedure for synthesis of compound 26a—N-Allyl-N-Boc-Tyr-OMe (26a):

N-Allyl-Tyr-OMe (24a) (0.58 g, 2.5 mmol) was reacted with Boc$_2$O (0.60 g, 27.5 mmol) in dioxane (15 mL) containing Et$_3$N (0.38 mL, 2.75 mmol) at room temperature for over night. After removal of solvent, the residue was extracted with AcOEt (60 mL), and the extract was washed with 10% citric acid (3×10 mL), 5% NaHCO3 (3×10 mL), and saturated NaCl (3×10 mL), dried over Na$_2$SO$_4$, filtered, and concentrated under reduced pressure. The residue was purified by flush chromatography (SiO$_2$, AcOEt:hexane=1:3) to give pure N-allyl-N-Boc-Tyr-OMe (26a) 0.58 g (69.4%), oil, $R_f$=0.82 (AcOEt:hexane=1:1), $[\alpha]_D^{25}$ −13.48° (c 0.83, MeOH). $^1$H NMR (400 MHz, CDCl$_3$) δ: 7.1-6.97 (m, 2H), 6.8-6.7 (m, 2H), 5.65-5.44 (m, 1.3H), 5.01 (d, 2H, J=14.52 Hz), 4.47-4.37 (m, 0.3H), 4.0-3.85 (m, 1.2H), 3.8-3.62 (m, 3.3H), 3.46-3.36 (m, 0.4H), 3.27-3.03 (m, 2.5H), 1.45 (s, 9H).

Example 10

This example illustrates the general procedure for synthesis of compound 26b—N-Allyl-N-Boc-Dmt-OMe (26b):

N-Allyl-Dmt-OMe (24b) (1.53 g, 5.79 mmol) was reacted with Boc$_2$O (1.39 g, 6.37 mmol) in dioxane (30 mL) containing Et$_3$N (0.89 mL, 6.37 mmol) at room temperature for over night. After removal of solvent, the residue was extracted with AcOEt (100 mL), and the extract was washed with 10% citric acid (2×15 mL), 5% NaHCO3 (2×15 mL), and saturated NaCl (2×15 mL), dried over Na$_2$SO$_4$, filtered, and concentrated under reduced pressure. The residue was purified by flush chromatography (SiO$_2$, AcOEt:hexane=1:1) to give pure N-allyl-N-Boc-Dmt-OMe (26b). Yield 1.12 g (53%), oil, $R_f$=0.65 (AcOEt:hexane=1:1); $[\alpha]_D^{25}$ −174.46° (c=0.49, MeOH). $^1$H NMR (400 MHz, DMSO-d$_6$) δ: 8.98 (s, 1H), 6.41 (s, 2H), 5.4-5.2 (m, 1H), 5.0-4.83 (m, 2H), 3.96-3.83 (m, 1H), 3.80-3.53 (m, 4H), 3.22-2.96 (m, 3H), 2.12 (s, 6H), 1.36 (s, 9H).

Example 11

This example illustrates the general procedure for synthesis of compound 27a—N-Allyl-N-Boc-Tyr-OH (27a):

1 N NaOH (9.33 mL, 9.33 mmol) was added to a solution of N-allyl-N-Boc-Tyr-OMe (26a) (1.36 g, 4.05 mmol) in MeOH (10 mL) at 0° C. After stirring at 0° C. for 20 min, the solution was stirred at room temperature over night. The MeOH was removed under vacuum, and the pH of the residue was adjusted to 3 with 10% citric acid. The resulted precipitate was extracted with AcOEt (2×40 mL), and the combined extract was washed with saturated NaCl solution (2×20 mL), dried over Na$_2$SO$_4$, filtered, and concentrated in vacuum to give a clear oil. Yield 1.09 g (84%), $R_f$=0.70 (AcOEt:MeOH=10:1), $[\alpha]_D^{25}$ −153.2° (c=0.83, MeOH). $^1$H NMR (400 MHz, DMSO-d$_6$) δ: 12.55 (s, 1H), 9.17 (s, 1H), 6.95 (d, 2H, J=8.4 Hz), 6.83-6.58 (m, 2H), 5.54-5.35 (m, 1H), 5.01-4.87 (m, 2H), 4.35-4.24 (m, 0.36H), 4.05-3.95 (m, 0.57H), 3.79-3.60 (m, 1H), 3.35-3.25 (m, 0.5H), 3.18-2.87 (m, 2.57H), 1.35 (s, 9H).

Example 12

This example illustrates the general procedure for synthesis of compound 27b—N-Boc-N-allyl-Dmt-OH (27b):

1 N NaOH (7.15 mL, 7.15 mmol) was added to a solution of N-allyl-N-Boc-Dmt-OMe (26b) (1.04 g, 2.86 mmol) in MeOH (10 mL) at 0° C. After stirring at 0° C. for 20 min, the solution was stirred at room temperature over night. The MeOH was removed under vacuum, and the pH of the residue was adjusted to 3 with 10% citric acid. The resulted precipitate was extracted with AcOEt (2×40 mL), and the combined extract was washed with saturated NaCl solution (2×20 mL), dried over Na$_2$SO$_4$, filtered, and concentrated in vacuum. The residue was purified by flash chromatography (SiO$_2$, AcOEt:hexane=1:1) to give the title compound. Yield 0.83 g (83%), mp 150-152° C.; $R_f$=0.35 (AcOEt:hexane=1:1); $[\alpha]_D^{25}$ −185.8° (c=0.61, MeOH). $^1$H NMR (400 MHz, CDCl$_3$) δ: 6.52 (s, 2H), 5.56-5.35 (m, 1H), 5.0-4.85 (m, 2H), 4.1-3.8 (m, 2H), 3.5-2.8 (m, 3H), 2.24 (s, 6H), 1.48 (s, 9H).

Example 13

This example illustrates the general procedure for synthesis of compound 28—[N,N-Diallyl-Tyr$^1$]EM-2 (28):

Boc-Pro-Phe-Phe-NH$_2$ (220 mg, 0.433 mmol) was treated with 6.7 mol/L HCl/dioxane (1.3 mL, 8.66 mmol) to remove the Boc group at room temperature for 30 minutes. The product was precipitated with ether, filtered and dried at vacuum. The resulted hydrochloride salt was dissolved in DMF (10 ml) containing DIPEA (0.19 mL, 1.09 mmol), and to this solution N,N-diallyl-Tyr-OH (25a) (0.124 g, 0.476 mmol) and PyBop (0.26 g, 0.5 mmol) were added. The reaction mixture was stirred at 0° C. for 10 min, then room temperature for 4 hours. After remove of solvent, the residue was diluted with AcOEt (80 mL). The dilution was washed with ice cold 10% citric acid (3×10 ml), 5% Na$_2$CO$_3$ (3×10 ml) and saturated NaCl (3×10 ml), dried over Na$_2$SO$_4$ and evaporated to dryness. The residue was purified by flash chromatography (SiO$_2$, AcOEt:MeOH=10:1). The compound was precipitated with hexane, filtered and dried under vacuum. The solid was dissolved in MeOH, and TFA (36 μl, 0.472 mmol) was added. After concentrated to dryness, the residue was purified by semi-preparative HPLC, and the purified peptide was lyophilized from 1 N HCl (3×0.32 mL) to give amorphous powder. Yield 220 mg (73.8%), mp 134-136° C., $[\alpha]_D$ –30.08° (c=0.57, H$_2$O), t$_R$ 16.4 min, [M+1]$^+$ 653. $^1$H NMR (400 MHz, DMSO-d$_6$) δ: 9.5 (br, 0.92H), 8.40 (d, 0.37H, J=7.95 Hz), 8.15 (d, 0.4H, J=8.15 Hz), 8.11 (d, 0.53H, J=8.22 Hz), 7.99 (d, 0.51H, J=7.76 Hz), 7.4-7.05 (m, 13.32H), 6.94 (d, 0.89H, J=8.44 Hz), 6.76 (d, 0.89H, J=8.44 Hz), 6.69 (d, 1.1H, J=8.42 Hz), 6.15-5.97 (m, 1H), 5.86-5.72 (m, 1H), 5.70-5.30 (m, 4H), 4.5-4.28 (m, 2.6H), 4.15-3.2 (m, 7.28H), 3.2-2.73 (m, 5.62H), 2.23 (br, 0.46H), 1.9-1.8 (m, 0.54H), 1.67-1.1 (m, 4H). $^{13}$C NMR δ: 172.54, 172.50, 170.56, 170.46, 170.29, 170.21, 156.84, 156.39, 137.83, 137.72, 137.70, 137.59 (12q), 130.62, 130.41, 129.13, 129.09, 129.01, 128.00, 127.96, 127.94, 127.90, 126.31, 126.13, 115.41, 115.26, 63.46, 62.03, 59.85, 59.20, 54.82, 54.43, 53.84, 53.74 (21t), 53.26, 46.80, 46.54, 37.38, 37.21, 36.88, 33.68, 32.74, 30.98, 28.63, 23.99, 21.14 (12s).

Example 14

This example illustrates the general procedure for synthesis of compound 29—[N,N-Diallyl-Dmt$^1$]EM-2 (29):

Boc-Pro-Phe-Phe-NH$_2$ (220 mg, 0.433 mmol) was treated with 7.7 mol/L HCl/dioxane (1.12 mL, 8.66 mmol) to remove the Boc group at room temperature for 30 minutes. The product was precipitated with ether, filtered and dried at vacuum. The resulted hydrochloride salt was dissolved in DMF (10 ml) containing DIPEA (0.19 mL, 1.09 mmol), and to this solution N,N-diallyl-Dmt-OH (25b) (0.138 g, 0.476 mmol) and PyBop (0.26 g, 0.5 mmol) were added. The reaction mixture was stirred at 0° C. for 10 min, then room temperature for 4 hours. After remove of solvent, the residue was diluted with AcOEt (80 mL). The dilution was washed with ice cold 10% citric acid (3×10 ml), 5% Na$_2$CO$_3$ (3×10 ml) and saturated NaCl (3×10 ml), dried over Na$_2$SO$_4$ and evaporated to dryness. The residue was purified by flash chromatography (SiO$_2$, AcOEt:MeOH=15:1). The compound was precipitated with hexane, filtered and dried under vacuum. The solid was dissolved in water, and lyophilized from 1 N HCl (3×0.31 mL) to give an amorphous powder. Yield 200 mg (71.3%), mp 151-153° C., $[\alpha]_D$ –15.6°(c=0.44, H$_2$O), t$_R$ 17.28 min, [M+1]$^+$ 681. $^1$H NMR (400 MHz, DMSO-d$_6$) δ: 10.60 (br, 1H), 9.50-9.05 (m, 1H), 8.42 (br, 1H), 8.19 (br, 1H), 7.99 (br, 1H), 7.44 (s, 1H), 7.37-6.98 (m, 12H), 6.47-6.40 (m, 2H), 6.20-5.25 (m, 6H), 4.46-4.28 (m, 2.3H), 4.17-3.70 (m, 3.4H), 3.4-3.17 (m, 2.8H), 3.15-2.74 (m, 6.7H), 2.26-1.94 (m, 6.5H), 1.8-1.2 (m, 4.3H). $^{13}$C NMR δ: 172.55, 170.66, 170.32, 170.25, 156.03, 138.45, 138.42, 138.02, 137.62, 137.54 (10q), 129.11, 129.07, 128.96, 127.97, 127.93, 127.87, 126.24, 126.10, 115.17, 115.05, 60.77, 58.87, 55.12, 54.04, 53.80, 53.25 (16t), 46.99, 45.99, 37.45, 36.69, 31.33, 28.67, 27.71, 23.88, 21.17 (9s), 20.23, 19.76 (2p).

Example 15

This example illustrates the general procedure for synthesis of compound 30—[N-Boc-N-allyl-Tyr]EM-2 (30):

Boc-Pro-Phe-Phe-NH$_2$ (220 mg, 0.433 mmol) was treated with 6.7 mol/L HCl/dioxane (1.3 mL, 8.66 mmol) to remove the Boc group at room temperature for 30 minutes. The product was precipitated with ether, filtered and dried at vacuum. The resulted hydrochloride salt was dissolved in DMF (10 ml) containing DIPEA (0.19 mL, 1.09 mmol), and to this solution N-allyl-N-Boc-Tyr-OH (27a) (0.153 g, 0.476 mmol) and PyBop (0.26 g, 0.5 mmol) were added. The reaction mixture was stirred at 0° C. for 10 min, then room temperature for 4 hours. After remove of solvent, the residue was diluted with AcOEt (80 mL). The dilution was washed with ice cold 10% citric acid (3×10 ml), 5% Na$_2$CO$_3$ (3×10 ml) and saturated NaCl (3×10 ml), dried over Na$_2$SO$_4$ and evaporated to dryness. The residue was purified by flash chromatography (SiO$_2$, AcOEt). The compound was precipitated with hexane, filtered and dried under vacuum. Yield 0.247 g (80%), mp 121-122° C., R$_f$=0.42 (AcOEt), $[\alpha]_D^{25}$ –75.14 (c=0.58, MeOH). $^1$H NMR (400 MHz, DMSO-d$_6$) δ: 9.2-9.0 (m, 1H), 8.0-7.9 (m, 1H), 7.82 (t, 1H, J=8.15 Hz), 7.3-7.1 (m, 12H), 6.94 (d, 2H, J=8.03 Hz), 6.7-6.57 (m, 2H), 5.73-5.58 (m, 1H), 5.08-4.93 (m, 2.5H), 4.83-4.72 (m, 0.5H), 4.5-4.37 (m, 2H), 4.17-4.07 (m, 1H), 3.94-3.82 (m, 0.6H), 3.82-3.7 (m, 0.4H), 3.63-3.37 (m, 2H), 3.35-3.18 (m, 1H), 3.14-2.96 (m, 2H), 2.93-2.63 (m, 4H), 1.9-1.57 (m, 4H), 1.3-1.05 (m, 9H). $^{13}$C NMR δ: 172.48, 171.31, 170.47, 169.25, 168.72, 155.75, 155.58, 154.36, 153.45, 137.82, 137.72 (11q), 134.70, 134.15, 130.28, 130.05, 128.98, 127.99, 127.89 (7t), 127.64, 127.27 (2q), 126.16, 126.1 (2t), 116.09, 115.98 (2s), 114.77, 114.69, 60.03, 58.04, 56.27, 54.08, 53.98, 53.74 (8t), 46.31, 46.13, 45.42, 44.67, 37.27, 36.73, 36.67, 33.68, 28.58 (9s), 27.73, 27.41 (2p), 23.98 (s).

Example 16

This example illustrates the general procedure for synthesis of compound 31—[N-Allyl-N-Boc-Dmt$^1$]EM-2 (31):

Boc-Pro-Phe-Phe-NH$_2$ (220 mg, 0.433 mmol) was treated with 7.7 mol/L HCl/dioxane (1.12 mL, 8.66 mmol) to remove the Boc group at room temperature for 30 minutes. The product was precipitated with ether, filtered and dried at vacuum. The resulted hydrochloride salt was dissolved in DMF (10 ml) containing DIPEA (0.19 mL, 1.09 mmol), and to this solution N-allyl-N-Boc-Dmt-OH (27b) (0.166 g, 0.476 mmol) and PyBop (0.26 g, 0.5 mmol) were added. The reaction mixture was stirred at 0° C. for 10 min, then room temperature for 4 hours. After remove of solvent, the residue was diluted with AcOEt (80 mL). The dilution was washed with ice cold 10% citric acid (3×10 ml), 5% Na$_2$CO$_3$ (3×10 ml) and saturated NaCl (3×10 ml), dried over Na$_2$SO$_4$ and evaporated to dryness. The residue was purified by flash chromatography (SiO$_2$, AcOEt:MeOH=30:1). The compound was precipitated with hexane, filtered and dried under vacuum. Yield 225 mg (70%), mp 131-133° C., R$_f$=0.7 (AcOEt:MeOH=10:1), $[\alpha]_D$ –82.9° (c=0.51, MeOH). $^1$H NMR (400 MHz, DMSO-d$_6$) δ: $^1$H NMR (400 MHz, DMSO-d$_6$) δ: 9.14 (s, 0.6H), 8.53 (s, 0.6H), 8.09 (s, 0.7H), 7.78-7.47 (m, 0.9), 7.47-6.85 (m, 11H), 6.85-6.16 (m, 2.4H), 6.1-5.4 (m, 1.1H), 5.35-4.92 (m, 2H), 4.92-4.50 (m, 1.8H), 4.4-3.6 (m, 4.6H), 3.6-2.46 (m, 6.6H), 2.4-1.9 (m, 3.9H), 1.9-0.9 (m, 15.9H). $^{13}$C NMR δ: 175.05, 174.41, 173.45, 172.39, 156.01, 155.59, 149.35, 138.43 (8q), 137.38 (t), 135.46 (q), 129.80, 129.40, 129.06, 128.45, 127.11, 126.80 (6t), 123.42 (q), 115.90 (t), 114.84 (s), 114.64 (t), 80.13 (q), 59.08, 58.48, 57.67, 54.35 (4t), 47.12, 46.20, 37.11, 34.39, 30.70 (5s), 28.61, 28.36 (2p), 25.77, 25.58 (2s), 19.40 (p).

Example 17

This example illustrates the general procedure for synthesis of compound 32—[N-Allyl-Tyr$^1$]EM-2 (32)

[N-Allyl-N-Boc-Tyr$^1$]EM-2 (30) (0.147 g, 0.206 mmol) was treated with TFA (0.32 mL, 4.13 mmol) and anisole (32 μL) for 30 min at room temperature. The reaction solution was diluted with hexane, the solid was collected by filter, dried over KOH pellets and purified by semi-preparative RP-HPLC. The purified peptide was lyophilized from 1 N HCl (3×0.2 mL) to give amorphous powder. Yield 113 mg (84%), mp 157-159° C., $[\alpha]_D$ –20.68° (c=0.46, H$_2$O), $t_R$ 15.2 min, [M+1]$^+$ 613. $^1$H NMR (400 MHz, DMSO-d$_6$) δ: 9.78 (br, 1H), 9.59 (s, 0.55H), 9.44 (s, 0.45H), 9.12 (br, 1H), 8.38 (d, 0.5H, J=8.57 Hz), 8.26 (d, 0.5H, J=8.26 Hz), 8.15 (d, 0.45H, J=8.30 Hz), 8.02 (d, 0.42H, J=7.85 Hz), 7.5-7.08 (m, 13H), 6.92 (d, 1H, J=8.40 Hz), 6.75 (d, 1H, J=8.37 Hz), 6.69 (d, 1H, J=8.42 Hz), 5.95-5.7 (m, 1H), 5.41-5.22 (m, 2H), 4.57-4.32 (m, 2.4H), 4.13 (br, 0.42H), 3.55-3.08 (m, 5H), 3.08-2.52 (m, 6H), 1.97-1.83 (m, 0.44H), 1.7-1.2 (m, 3.63H). $^{13}$C NMR δ: 172.65, 172.57, 170.48, 170.45, 170.40, 169.81, 165.84, 165.81, 156.72, 156.47, 137.92, 137.73, 137.47 (13q), 130.92, 130.84, 129.14, 129.11, 129.09, 128.75, 127.99, 127.97, 127.94, 127.88, 126.64, 126.20, 124.35, 123.42 (14t), 122.39, 121.98 (2s), 115.41, 115.15, 59.59, 59.19, 58.98, 58.38, 54.52, 54.18, 53.78, 53.75 (10t), 48.06, 47.83, 46.63, 46.40, 37.45, 37.38, 37.10, 35.58, 34.83, 31.11, 28.84, 24.09, 21.17 (13s).

Example 18

This example illustrates the general procedure for synthesis of compound 33—[N-Allyl-Dmt$^1$]EM-2 (33):

[N-Allyl-N-Boc-Dmt$^1$]EM-2 (31) (0.11 g, 0.149 mmol) was treated with TFA (0.23 mL, 2.97 mmol) and anisole (30 µL) for 30 min at room temperature. The reaction solution was diluted with hexane, the solid was collected by filter, dried over KOH pellets and purified by semi-preparative RP-HPLC. The purified peptide was lyophilized from 1 N HCl (3×0.13 mL) to give amorphous powder. Yield 72 mg (71.6%), mp 170-172° C., $[\alpha]_D$ –5.86° (c=0.42, H$_2$O), $t_R$ 15.82 min, [M+1]$^+$ 641. $^1$H NMR (400 MHz, DMSO-d$_6$) δ: 9.82 (br, 0.84H), 9.34-9.10 (m, 1.9H), 8.33 (d, 0.83H, J=8.54 Hz), 8.12 (d, 0.82H, J=8.34 Hz), 8.01 (d, 0.16H, J=7.7 Hz), 7.96 (d, 0.16H, J=7.99 Hz), 7.43 (s, 0.90H), 7.35-7.13 (m, 10.67H), 7.09 (s, 0.84H), 6.47-6.40 (m, 2H), 5.97-5.70 (m, 1H), 5.44-5.19 (m, 2H), 4.5-4.33 (m, 2.2H), 4.09 (br, 0.16H), 3.65-3.45 (m, 0.48H), 3.35-2.70 (m, 11.2H), 2.2-2.0 (m, 6H), 1.7-1.1 (m, 4H). $^{13}$C NMR δ: 172.60, 170.58, 170.31, 170.14, 169.93, 166.40, 155.86, 155.62, 138.50, 138.20, 137.97, 137.63, 137.58, 137.51 (14q), 129.12, 129.10, 128.91, 128.75, 128.03, 127.96, 127.92, 127.85, 126.44, 126.09 (10t), 121.94, 120.44 (2s), 115.02 (t), 58.92, 56.22, 55.65, 54.76, 53.91, 53.60 (6t), 58.92, 56.22, 55.65, 54.76, 53.91, 53.60 (6t), 47.66, 46.64, 37.53, 36.85, 31.20, 29.66, 24.90, 21.11 (8s), 20.11, 19.35 (2p)

Example 19

This example illustrates the general procedure for synthesis of compound 34—Bis(N-allyl-N-Boc-Dmt-NH)-hexyl (34):

To a solution of diaminohexane (33 mg, 0.286 mmol) in DMF (10 mL), N-allyl-N-Boc-Dmt-OH (27b) (200 mg, 0.572 mmol), DIPEA (119 µL, 0.687 mmol), and PyBop (313 mg, 0.60 mmol) were added. The reaction mixture was stirred at 0° C. for 10 min, then room temperature for 4 hours. After removal of solvent, the residue was extract with AcOEt (50 mL). The organic phase was washed with ice cold 10% citric acid (3×10 mL), 5% Na$_2$CO$_3$ (3×10 mL) and saturated aqueous NaCl (3×10 mL), dried over Na$_2$SO$_4$ and evaporated to dryness. The residue was purified by flash chromatography (SiO$_2$, AcOEt:hexane=2:1), and the compound was precipitated with hexane, filtered and dried in vacuo. Yield 132 mg (59.2%), mp 90-92° C., $[\alpha]_D$ –57.60 (c=0.32, MeOH), R$_f$=0.65 (EtOAC:hexane=2:1). $^1$H NMR (400 MHz, CDCl$_3$) δ: 8.04 (s, 1.3H), 7.45 (br, 0.14H), 7.13 (br, 0.14H), 6.53 (s, 4H), 5.9-5.5 (m, 4H), 5.2-5.05 (m, 4H), 4.5-3.9 (m, 6H), 3.5-3.1 (m, 4H), 3.1-2.6 (m, 4H), 2.27 (s, 12H), 1.6-1.4 (m, 18H), 1.3-0.5 (m, 8H). $^{13}$C NMR δ: 171.42, 170.75, 156.43, 154.73, 154.10, 138.44 (6q), 135.63 (t), 126.34 (q), 115.64 (s), 115.39, 115.04 (2t), 81.50 (q), 59.25 (t), 46.87, 39.15, 29.89, 28.81 (4s), 28.38 (p), 26.29 (s), 20.31 (p).

Example 20

This example illustrates the general procedure for synthesis of compound 35—Bis(N-allyl-Dmt)-hexyl (35):

Bis(N-allyl-N-Boc-Dmt-amino)-hexyl (34) (76 mg, 0.097 mmol) was treated with TFA (0.15 mL, 1.9 mmol) and anisole (20 µL) for 30 min at room temperature. The reaction solution was diluted with hexane and the solid was collected by filtration, dried over KOH pellets and purified by semi-preparative RP-HPLC. The purified peptide was lyophilized from water containing 1 N HCl (0.1 mL) for three times to give an amorphous powder. Yield 36.4 mg (57.3%), mp 174-176° C., $[\alpha]_D$ 54.95°(c=0.36, H$_2$O), $t_R$ 15.43 min, [M+1]$^+$ 580. $^1$H NMR (400 MHz, DMSO-d$_6$) δ: 9.07 (s, 2H), 8.02 (br, 2H), 6.39 (s, 4H), 5.95-5.84 (m, 2H), 5.46-5.30 (m, 4H), 3.72-3.60 (m, 2H), 3.48-3.35 (m, 4H), 3.05-2.93 (m, 6H), 2.92-2.80 (m, 2H), 2.17 (s, 12H), 1.2-1.02 (m, 4H), 0.96-0.82 (m, 4H). $^{13}$C NMR δ: 165.4, 155.46, 140.33, 138.11 (4q), 129.50 (t), 122.11 (s), 114.76, 58.27 (2t), 47.54, 38.52, 29.59, 28.29, 25.71 (5s), 19.93 (p).

Example 21

This example illustrates the general procedure for synthesis of compound 36—3,6-Bis(N-Allyl-N-Boc-Dmt-aminopropyl)-2(1H)-pyrazinone (36):

3,6-Bis(Z-aminopropyl)-2(11H)-pyrazinone (141 mg, 0.286 mmol) was stirred in 25% HBr/HOAc (0.96 mL, 4 mmol) with an ice bath for 10 min then room temperature for 3 hr. The resulting amine was precipitated with ether and dried in vacuo. The precipitate was dissolved in DMF (10 mL) containing DIPEA (240 µL, 1.37 mmol), to which N-allyl-N-Boc-Dmt-OH (27b) (200 mg, 0.572 mmol) and PyBop (312 mg, 0.60 mmol) were added. The solution was first stirred in an ice bath for 10 min, then at room temperature for 4 h. After removal of the solvent in vacuo, the residue was extracted with AcOEt (30 mL), which was washed with 10% citric acid (2×10 mL), 5% NaHCO$_3$ (2×10 mL), and saturated aqueous NaCl solution (2×10 mL), dried over Na$_2$SO$_4$, filtered, and evaporated in vacuo. The result residue was purified by flash chromatography (SiO$_2$, AcOEt:MeOH=10:1) and the compound was precipitated with ether. Yield 109 mg (43%), mp 122-124° C., $[\alpha]_D$ –57° (c=0.31, MeOH), R$_f$=0.59 (EtOAC:MeOH=10:1). $^1$H NMR (400 MHz, CDCl$_3$) δ: 12.0 (br, 1H), 7.6 (br, 2H), 6.7-6.1 (m, 6H), 5.9-5.7 (m, 2H), 5.2-5.0 (m, 4H), 4.55-4.30 (m, 1.5H), 4.2-3.8 (m, 4H), 3.5-2.58 (m, 9.6H), 2.58-2.0 (m, 18H), 1.9-1.2 (m, 22H). $^{13}$C NMR δ: 171.74, 171.39, 156.73, 155.88, 155.35, 154.76, 154.40, 138.57, 138.34 (9q), 135.43, 135.32 (2t), 129.54, 126.28, 125.68 (3q), 116.04 (s), 115.39 (t), 81.07, 80.76 (2q), 59.14 (t), 47.81, 39.27, 38.14, 29.32, 29.26 (5s), 28.38 (p), 27.99, 26.68, 25.42 (3s), 20.24, 18.26 (2p).

Example 22

This example illustrates the general procedure for synthesis of compound 37—3,6-Bis(N-allyl-Dmt-aminopropyl)-2(1H)-pyrazinone (37):

3,6-Bis(N-allyl-N-Boc-Dmt-aminopropyl)-pyrazinone (36) (57 mg, 0.064 mmol) was treated with TFA (0.15 mL, 1.9 mmol) and anisole (15 μL) for 30 min at room temperature. The reaction solution was diluted with hexane and the solid was collected by filtration, dried over KOH pellets and purified by semi-preparative RP-HPLC. The purified peptide was lyophilized from water containing 1N HCl (0.1 mL) for three times to give an amorphous powder. Yield 31.4 mg (64.6%), mp 213-215° C., $[\alpha]_D$ 32.07°(c=0.36, $H_2O$), $t_R$ 11.68 min, $[M+1]^+$ 588. $^1$H NMR (400 MHz, DMSO-$d_6$) δ: 9.99 (br, 2H), 9.33 (br, 2H), 9.07 (br, 2H), 8.23 (t, 1H, J=4.77 Hz), 8.15 (t, 1H, J=4.52 Hz), 5.98-5.85 (m, 2H), 5.50-5.32 (m, 4H), 3.8-3.4 (m, 6H), 3.13-2.85 (m, 8H), 2.47-2.42 (m, 2H), 2.3-2.05 (m, 17H), 1.7-1.38 (m, 4H). $^{13}$C NMR δ: 166.81, 166.70, 155.57, 155.52, 155.40, 138.20 (6q), 128.54, 128.45 (2t), 122.78, 122.68 (2s), 121.69, 121.64 (2q), 114.82, 57.90, 57.86 (3t), 47.28, 38.59, 38.20, 29.26, 29.17, 28.96, 27.17, 25.42 (8s), 19.90, 19.87, 17.97 (3p).

Example 23

This example illustrates the general procedure for the synthesis of the compounds of examples 1 and 2, as depicted in Scheme 1 and Scheme 2:

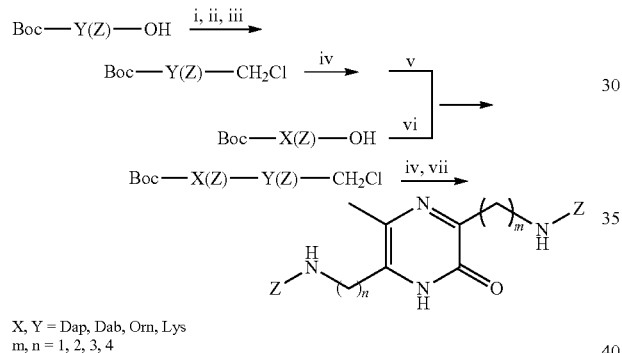

X, Y = Dap, Dab, Orn, Lys
m, n = 1, 2, 3, 4

The reagents and conditions for Scheme 1 are:
(i) IBCF, $Et_3N$, THF, −15° C./10 min
(ii) $CH_2N_2/Et_2O$, room tempt./12 h;
(iii) HCl/dioxane/15 min; (iv) HCl/dioxane;
(v) $Et_3N$, DMF; (vi) IBCF, $Et_3N$, THF; and
(vii) MeOH reflux conditions for 1, wherein X and Y can be the different or the same and each of X and Y is Dap, Dab, Orn, and Lys; and wherein "m" and "n" are the same or different and each of "m" and "n" is from 1 to about 4.

Scheme 2

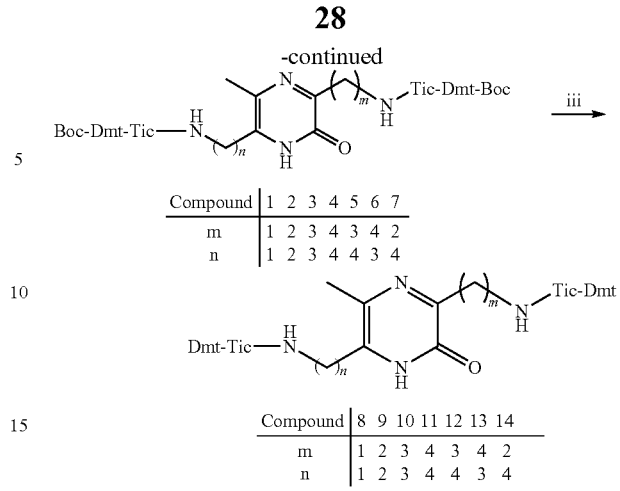

| Compound | 1 | 2 | 3 | 4 | 5 | 6 | 7 |
|---|---|---|---|---|---|---|---|
| m | 1 | 2 | 3 | 4 | 3 | 4 | 2 |
| n | 1 | 2 | 3 | 4 | 4 | 3 | 4 |

| Compound | 8 | 9 | 10 | 11 | 12 | 13 | 14 |
|---|---|---|---|---|---|---|---|
| m | 1 | 2 | 3 | 4 | 3 | 4 | 2 |
| n | 1 | 2 | 3 | 4 | 4 | 3 | 4 |

The reagents and conditions for Scheme 2 are:
(i) 25% HBr/AcOH;
(ii) Boc-Dmt-Tic-OH, DIPEA, PyBop, DMF; and
(iii) TFA/anisole, wherein "m" and "n" are the same or different and each of "m" and "n" is from 1 to about 20.

Example 24

This example illustrates the general procedure for the synthesis of the compounds of examples 3 and 4, as depicted in Scheme 3:

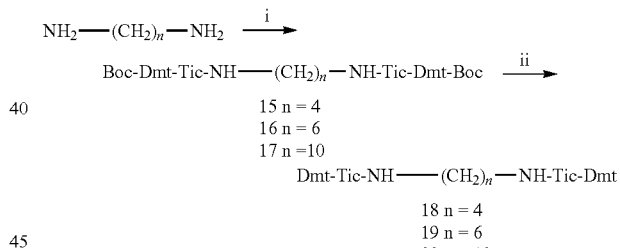

The reagents and conditions for Scheme 1 are:
(i) Boc-Dmt-Tic-OH, DIPEA, PyBop, DMF; and
(ii) TFA/anisole, wherein "m" and "n" are the same or different and each of "m" and "n" is from 1 to about 20.

Example 25

This example illustrates the general procedure for the synthesis of the compounds of example 4, as depicted in Scheme 4:

Scheme 4

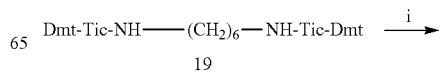

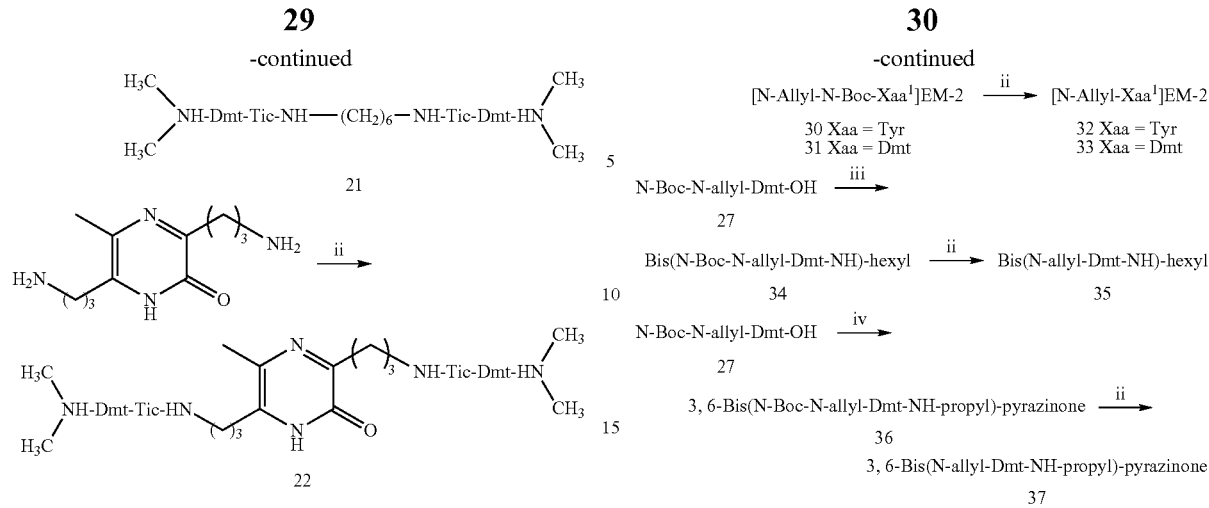

21

22

The reagents and conditions for Scheme 4 are:
(i) 37% HCHO, NaBH$_3$CN, and
(ii) N,N-Dimethyl-Dmt-Tic-OH, DIPEA, PyBop, DMF.

Example 26

This example illustrates the general procedure for synthesis of the compounds of examples 5-12, as depicted in Scheme 5.

Scheme 5

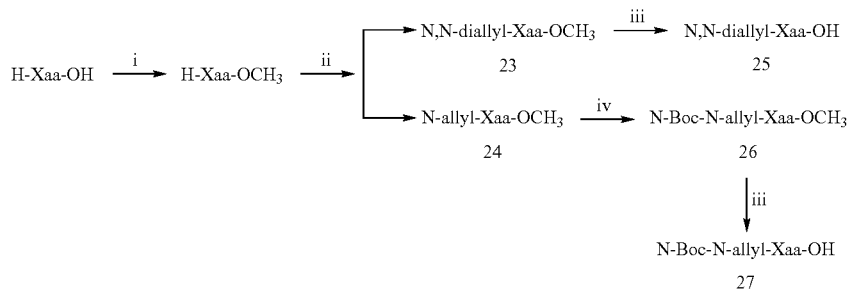

(Xaa = a: Tyr; b: Dmt)

The reagents and conditions for Scheme 5 are:
(i) SOCl$_2$/MeOH;
(ii) allyl-Br, DIPEA, MeOH, 50° C., 5 h;
(iii) 1 N NaOH; and
(iv) (Boc)$_2$O, Et$_3$N, dioxane,
wherein Xaa is Tyr or Dmt.

Example 27

This example illustrates the general procedure for synthesis of the compounds of examples 13-22, as depicted in Scheme 6.

Scheme 6

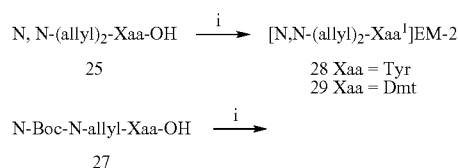

[N-Allyl-N-Boc-Xaa¹]EM-2 →ⁱⁱ→ [N-Allyl-Xaa¹]EM-2

30 Xaa = Tyr          32 Xaa = Tyr
31 Xaa = Dmt          33 Xaa = Dmt

N-Boc-N-allyl-Dmt-OH →ⁱⁱⁱ→

27

Bis(N-Boc-N-allyl-Dmt-NH)-hexyl →ⁱⁱ→ Bis(N-allyl-Dmt-NH)-hexyl 34                                     35

N-Boc-N-allyl-Dmt-OH →ⁱᵛ→

27

3,6-Bis(N-Boc-N-allyl-Dmt-NH-propyl)-pyrazinone →ⁱⁱ→

36

3,6-Bis(N-allyl-Dmt-NH-propyl)-pyrazinone

37

The reagents and conditions for Scheme 6 are:
(i) H-Pro-Phe-Phe-NH$_2$, DIPEA, PyBop, DMF;
(ii) TFA/anisole;
(iii) 1,6-diaminohexane, DIPEA, PyBop, DMF; and
(iv) 3,6-Bis(3'-aminopropyl)-pyrazinone, DIPEA, PyBop, DMF,
wherein Xaa is Tyr or Dmt Example 28

This example illustrates the general chemical synthesis of the compounds depicted in Schemes 1-4.

Optically pure 2',6'-dimethyl-L-tyrosine (Dmt) was prepared according to the method of Dygos et al., *Synthesis*, 8: 741-743 (1992). Boc-Dmt-Tic-OH, and N,N-dimethyl-Dmt-Tic-OH were prepared as described in Salvadori et al., *J. Med. Chem.*, 40: 3100-3108 (1997), and Salvadori et al., *J. Med. Chem.*, 42: 5010-5019 (1999), respectively. Fmoc-NH—(CH$_2$)$_6$—NH-Boc was prepared from Boc-NH—(CH$_2$)$_6$—NH$_2$ as described in Callahan et al., *J. Med. Chem.*, 32: 391-396 (1989). 3,6-Disubstituted-2(1H)-pyrazinone derivatives were synthesized following the procedure illustrated in the Examples in Scheme 1. Briefly, Boc-X(Z)-OH was coupled with H—Y(Z)-CH$_2$Cl by a mixed anhydride method to produce Boc-X(Z)-Y(Z)-CH$_2$Cl [X, Y=Dap (2,3-diaminopropionic acid), Dab (2,4-diaminobutyric acid), Orn, Lys]. After removal of the Boc group by HCl in dioxane, the corresponding amine hydrochloride in MeOH was treated under reflux conditions for one hour to produce the Z-protected pyrazinone derivative. As shown in the Examples in Scheme 2, the Z-protecting group was then removed by HBr/HOAc to release the amine group, which was then coupled with Boc-Dmt-Tic-OH using PyBop reagent to produce Boc-protected 3,6-bis(Dmt-Tic-aminoalkyl)-pyrazinone derivatives (1-7). The Boc group was removed by TFA/anisole to give the 3,6-bis(Dmt-Tic-aminoalkyl)-pyrazinone derivatives (8-14).

Symmetric pharmacophore compounds linked with diaminoalkanes (18-20) were synthesized as shown in the Examples in Scheme 3. Boc-Dmt-Tic-OH was coupled with diaminoalkane to produce bis(Boc-Dmt-Tic-amino)-alkanes (15-17), which were then treated with TFA/anisole to give bis(Dmt-Tic-amino)-alkanes (18-20).

Compound 21 was prepared directly from 19 through reductive alkylation with formaldehyde and $NaBH_3CN$ in a $H_2O$ and $CH_3CN$ solution as shown in the Examples in Scheme 4. This method, however, failed in the preparation of compound 22 from compound 10. Thus, after reductive alkylation, the unique 365 nm fluorescence of compound 10 was quenched, and the molecular weight of reaction product was 4 mass units greater than the desired one, which suggested that the two double bonds in the pyrazinone ring were reduced. Therefore, N,N-dimethyl-Dmt-Tic-OH was prepared through reductive alkylation of H-Dmt-Tic-OH as reported (Salvadori et al., J. Med. Chem., 40: 3100-310* (1997)) and coupled with 3,6-bis(3'-aminopropyl)-pyrazinone by PyBop to give the desired compound (22).

The identification and purity of the final compounds were verified using MS, NMR, analytical HPLC, and elemental analysis. The elemental analysis data of the final compounds are summarized in Table 1. The compounds exhibiting greater than 98% purity were used for all biological assays.

Example 29

This example illustrates the general synthesis of the compounds depicted in Schemes 5-6.

Dmt was prepared according to the method of Dygos et al. 3,6-Bis-(aminopropyl)-2(1H)-pyrazinone was synthesized as reported in Jinsmaa et al., J. Med. Chem., 47: 2599 (2004), and the mono- and diallyl substituted Xaa (Xaa=Tyr and Dmt) as shown in the Examples in Scheme 1. The key intermediates of mono- and diallyl-substituted Xaa-$OCH_3$ (25 and 23) were prepared in one pot from allylbromide (2.5 eq) and H-Xaa-OMe in the presence of DIPEA (2.7 eq) under 50° C. for 5 h. N,N-(allyl)$_2$-Xaa-$OCH_3$ (23) was hydrolyzed to obtain N,N-(allyl)$_2$-Xaa-OH (24). $N^\alpha$—H of N-allyl-Xaa-$OCH_3$ (25) was protected with Boc group in THF to produce N-Boc-N-allyl-Xaa-$OCH_3$ (26), and then hydrolyzed with NaOH to N-Boc-N-allyl-Xaa-OH (27). Mono- and diallyl-Xaa residue substituted EM-2 was prepared in solution using Boc-protection methods. After deprotection of Boc-Pro-Phe-Phe-$NH_2$ with HCl/dioxane, the resulting amino component was condensed with N,N-(allyl)$_2$-Xaa-OH (24) or N-Boc-N-allyl-Xaa-OH (27) using PyBop as the coupling reagent to give compounds 28 and 30, and Boc protected compounds 29 and 31, respectively. Removal of the Boc-group of Boc-protected compounds 29 and 31 with TFA gave the final compounds 29 and 31. N-Boc-N-allyl-Dmt-OH (27b) was coupled with 1,6-hexanediamine or 3,6-bis-(aminopropyl)-2(1H)-pyrazinone to produce Boc-protected dimeric compounds, followed by removal of Boc group with TFA to give the final compounds 32 and 33.

Example 30

This example illustrates the protocol used to calculate melting points of the compounds described in the examples:

Melting points of the inventive compounds were determined on a Yanagimoto micromelting point apparatus and are uncorrected. TLC was performed on precoated plates of silica gel F254 (Merck, Darmstada, Germany). Rf values refer to the following solvent systems: (1) AcOEt:hexane=3:1, (2) AcOEtMeOH=10:1, (3) CHCl3:MeOH=10:1, (4) AcOEt: hexane=2-1, (5) n-BnOH:$H_2O$:AcOH=4:1:5, (6) n-BnOH:H2O:AcOH:pyridine=4:1:1:2. Optical rotations were determined with a DIP-1000 automatic polarimeter (Japan Spectroscopic Co.). Analytical RP-HPLC and semi-preparative RP-HPLC used is Waters Delta 600 with COSMOSIL CIS column (4.6 mm×250 mm) and COSMOSIL CIS column (20 mm×250 mm), respectively. The solvent for analytical HPLC was as follows: A, 0.05% TFA in water; B, 0.05% TFA in CH3CN. The column was eluted at a flow rate of 1 mL/min with a linear gradient of 90% A to 10% A in 30 min; the retention time is reported as Tr (min). Mass spectra were measured with a KRATOS MALDI-TOF (matrix-assisted laser desorption ionization time-of-flight mass spectrometry). $^1H$ and 13C NMR spectra were measured on a Bruker DPX-400 spectrometer at 25° C. Chemical shift values are expressed as ppm downfield from tetramethylsiliane.

Example 31

This example illustrates the assay used to measure opioid receptor binding affinity of the compounds described in the examples:

Opioid receptor affinities were determined under equilibrium conditions [2.5 hr at room temperature (23° C.)] in a competition assay using brain $P_2$ synaptosomal membranes prepared from Sprague-Dawley rats. Synaptosomes were preincubated to remove endogenous opioids, washed in excess ice-cold buffer containing protease inhibitor and stored in a glycerol-containing buffer with protease inhibitor at −80° C. as described in Lazarus et al., J. Med. Chem. 34:1350-55 (1991). The δ- and δ-opioid receptors were radiolabeled with [$^3H$]DPDPE or [$^3H$]deltorphin II and [$^3H$] DAMGO, respectively, and excess unlabeled peptide (2 μM) established the level of nonspecific binding. After incubation, the radiolabeled membranes were rapidly filtered on Whatman GF/C glass fiber filters presoaked in 0.1% polyethylenimine in order to optimize the signal-to-noise ratio, washed with ice-cold BSA buffer, and dried at 75-80° C. Radioactivity was determined using EcoLume (ICN, Costa Mesa, Calif.). All compounds were analyzed in duplicate using 5-8 peptide dosages and several synaptosomal preparations in independent repetitions to ensure statistical significance. The affinity constants (Ki) were calculated according to Cheng and Prusoff (Cheng et al., Biochem. Pharmacol., 22: 3099-3108 (1978)).

Example 32

This example illustrates the assay used to measure the δ- and μ-opioid biological activity of the compounds described in the examples in isolated tissue preparations:

The myenteric plexus longitudinal muscle preparations (2-3 cm segments) from the small intestine of male Hartley strain guinea pigs (GP1) measured μ-opioid receptor agonism and a single mouse vas deferens (MVD) was used to determine δ-opioid receptor agonism as described in Sasaki et al. Bioorg. Med. Chem., 11: 675-678 (2003). The isolated tissues were suspended in organ baths containing balanced salt solutions in a physiological buffer, pH 7.5. Agonists were tested for the inhibition of electrically evoked contraction and expressed as $IC_{50}$ (nM) obtained from the dose-response curves. The $IC_{50}$ values represent the mean±SE of five to six separate assays. δ-Antagonist potencies in the MVD assay were determined against the δ agonist deltorphin II, and μ antagonism in the GPI assay used the μ agonist endomorphin-2 and both are expressed as $pA_2$ using the Schild Plot (Arunlakshana et al. Brit. J. Pharmacol., 14: 48-58 (1959)).

Example 33

This example illustrates the binding affinity of the inventive Dmt-Tic analog compounds 8-14, and 18-22 using the rat brain membrane receptor binding affinity assay.

TABLE 1

| Compd. | Peptide | $K_i(\delta)(nM)^a$ | $n^c$ | $K_i(\mu)(nM)^b$ | $n^c$ | $K_i(\mu)/K_i(\delta)$ |
|---|---|---|---|---|---|---|
| 8 | Bis[(Dmt-Tic-NH)-methyl]-pyra | 0.163 ± 0.018 | (3) | 3.76 ± 0.3 | (4) | 23 |
| 9 | Bis[(Dmt-Tic-NH)-ethyl]-pyra$^d$ | 0.095 ± 0.0004 | (3) | 2.83 ± 0.12 | (3) | 30 |
| 10 | Bis[(Dmt-Tic-NH)-propyl]-pyra | 0.155 ± 0.016 | (3) | 3.08 ± 0.17 | (3) | 20 |
| 11 | Bis[(Dmt-Tic-NH)-butyl]-pyra | 0.323 ± 0.007 | (3) | 1.74 ± 0.14 | (5) | 5 |
| 12 | H-Dmt-Tic-propyl-pyra-butyl-Tic-Dmt-H | 0.16 ± 0.025 | (3) | 1.56 ± 0.11 | (3) | 10 |
| 13 | H-Dmt-Tic-butyl-pyra-propyl-Tic-Dmt-H | 0.092 ± 0.01 | (3) | 2.28 ± 0.03 | (3) | 25 |
| 14 | H-Dmt-Tic-ethyl-pyra-butyl-Tic-Dmt-H | 0.107 ± 0.007 | (3) | 1.37 ± 0.13 | (3) | 13 |
| 18 | Bis[Dmt-Tic-NH]-butyl | 0.124 ± 0.016 | (3) | 5.72 ± 0.22 | (3) | 46 |
| 19 | Bis[Dmt-Tic-NH]-hexyl | 0.129 ± 0.03 | (3) | 1.79 ± 0.08 | (3) | 14 |
| 20 | Bis[Dmt-Tic-NH]-decyl | 1.53 ± 0.16 | (3) | 4.86 ± 0.41 | (4) | 3 |
| 21 | Bis[N,N-dimethyl-Dmt-Tic-NH]-hexyl | 0.06 ± 0.01 | (4) | 2.21 ± 0.08 | (6) | 37 |
| 22 | 3,6-Bis[N,N-dimethyl-Dmt-Tic-NH-propyl]-pyra | 0.287 ± 0.015 | (3) | 1.68 ± 0.17 | (3) | 6 |

The data presented in Table 1 illustrates the high affinity the inventive Dmt analogs have for the δ-opioid receptor, and the dual affinity several of the compounds (e.g. 21, and 22) have with respect to the μ-opioid receptor.

In Table 1, "$a$" represents the opioid receptor binding affinity of DMT-Tic dimers versus [$^3$H]DAMGO.

In Table 1, "$b$" represents the opioid receptor binding affinity of DMT-Tic dimers versus [$^3$H]DPDPE.

In Table 1, "$c$" represents the number of independent repetitions which used different synaptosomal preparations.

In Table 1, "pyra$^d$" represents pyrazinone.

Example 34

This example illustrates the functional bioactivity of inventive Dmt-Tic analog compounds 8-14, and 18-22 using the MVD and GPI bioassays to test δ-opioid and μ-opioid bioactivity, respectively.

The data presented in Table 2 illustrates the dual δ- and μ-opioid antagonist activity of the inventive compounds, namely compounds 21 and 22. Further, the data illustrates the lack of opioid agonist activity associated with the inventive compounds.

In Table 2, "$a$" represents the data as means of over five independent repetitions used which used different isolated tissue preparations.

In Table 1, "$b$" by represents the functional bioactivity of DMT-Tic dimers versus deltorphin II as the agonist.

In Table 1, "$c$" represents the functional bioactivity of DMT-Tic dimers versus endomorphin-2.

In Table 1, "pyra$^d$" represents pyrazinone.

Example 35

This example illustrates the binding affinity of the inventive Dmt-derivatized endomorphin compounds 28-33, and 37 using the rat brain membrane receptor binding affinity assay.

TABLE 2

| | | MVD$^a$ | | GPI$^a$ | |
|---|---|---|---|---|---|
| Compound. | Peptide | agonist IC$_{50}$, nM | Antagoninst$^b$ pA$_2$ (nM) | agonist IC$_{50}$, nM | Antagonist pA$_2$ (nM) |
| 8 | Bis[(Dmt-Tic-NH)-methyl]-pyra$^d$ | >10000 | 11.22 (0.006) | >10000 | N.D |
| 9 | Bis[(Dmt-Tic-NH)-ethyl]-pyra | >10000 | 10.73 (0.0186) | >10000 | 6.78 (165) |
| 10 | Bis[(Dmt-Tic-NH)-propyl]-pyra | >10000 | 10.56 (0.0275) | 7025 ± 2467 | N.D. |
| 11 | Bis[(Dmt-Tic-NH)-butyl]-pyra | >10000 | 11.06 (0.0871) | >10000 | N.D |
| 12 | H-Dmt-Tic-propyl-pyra-butyl-Tic-Dmt-H | >10000 | 10.60 (0.0251) | >10000 | N.D |
| 13 | H-Dmt-Tic-butyl-pyra-propyl-Tic-Dmt-H | >10000 | 10.47 (0.0339) | >10000 | 6.95 (112) |
| 14 | H-Dmt-Tic-ethyl-pyra-butyl-Tic-Dmt-H | >10000 | 10.99 (0.0102) | >10000 | N.D |
| 18 | Bis[Dmt-Tic-NH]-butyl | >10000 | 10.51 (0.0309) | >10000 | 6.99 (102) |
| 19 | Bis[Dmt-Tic-NH]-hexyl | >10000 | 10.62 (0.024) | 2715 ± 1359 | N.D. |
| 20 | Bis[Dmt-Tic-NH]-decyl | >10000 | 10.97 (0.0107) | 5425 ± 1838 | N.D |
| 21 | 1,6-Bis(N,N-Dimethyl-Dmt-Tic-NH)-hexyl | >10000 | 11.28 (0.0052) | >10000 | 8.34 (4) |
| 22 | 3,6-Bis(N,N-dimethyl-Dmt-Tic-NH-propyl)-pyra | >10000 | 10.42 (0.038) | >10000 | 7.71 (19) |
| | H-Dmt-Tic-OH | none | 8.48 (3.0) | N.D | N.D |
| | Naltrindole$^{6a}$ | | 9.2 (0.631) | | 7.3 (50) |

TABLE 3

| Compound | Peptide | $K_i(\mu)$ (nM)[a] | n[c] | $K_i(\delta)$ (nM)[b] | n[c] | $K_i(\delta)/K_i(\mu)$ |
|---|---|---|---|---|---|---|
| 28 | [N,N-(allyl)$_2$]EM-2 | 1045 ± 175 | (6) | 5755 ± 1224 | (4) | 6 |
| 29 | [N-allyl]EM-2 | 130 ± 9.27 | (6) | 7358 ± 259 | (3) | 57 |
| 30 | [N,N-(allyl)$_2$Dmt$^1$]EM-2 | 13.1 ± 1.3 | (6) | 1416 ± 50 | (4) | 108 |
| 31 | [(N-allyl)Dmt$^1$]EM-2 | 0.45 ± 0.08 | (5) | 560 ± 49 | (4) | 1244 |
| 32 | Bis-[(N-allyl)Dmt-NH-propyl]pyrazinone | 12.4 ± 1.1 | (3) | 51.5 ± 4.1 | (3) | 4 |
| 33 | Bis-[(N-allyl)Dmt-NH]hexyl | 6.94 ± 1.4 | (3) | 77.8 ± 14 | (4) | 11 |
|  | EM-2[e] | 0.69 |  | 9230 |  | 13400 |
|  | [Dmt$^1$]EM-2[e] | 0.15 |  | 28.2 |  | 188 |
| 37 | 3,6-Bis-[Dmt-NH-propyl]pyrazinone[f] | 0.042 |  | 13.2 |  | 307 |
|  | H-Dmt[NH—(CH$_2$)$_6$—NH]Dmt-H[g] | 0.053 |  | 46.1 |  | 870 |

The data presented in Table 3 illustrates the high affinity the inventive Dmt derivative endomorphin compounds have for the μ-opioid receptor.

In Table 3, "[a]" represents the opioid receptor binding affinity of DMT-Tic dimers versus [$^3$H]DAMGO.

In Table 1, "[b]" represents the opioid receptor binding affinity of DMT-Tic dimers versus [$^3$H]DPDPE.

In Table 3, "[c]" represents the number of independent repetitions which used different synaptosomal preparations.

In Table 3, "pyra[d]" represents pyrazinone.

Example 36

This example illustrates the functional bioactivity of inventive Dmt-derivatized endomorphin compounds 30-33 using the MVD and GPI bioassays to test δ-opioid and μ-opioid bioactivity, respectively.

TABLE 4

| Peptide | GPI, nM | pA$_2$[a] | MVD, nM | pA$_2$[b] | pA$_2$(μ)/pA$_2$(δ) |
|---|---|---|---|---|---|
| 30 [N,N-(allyl)$_2$-Dmt$^1$]EM-2 | >10000 | None | >10000 | 6.13 | — |
| 31 [N-allyl-Dmt$^1$]EM-2 | >10000 | 8.59 | >10000 | 6.32 | 239 |
| 32 3,6-Bis-[(N-allyl)Dmt-NH-propyl]pyrazinone | >10000 | 7.17 | >10000 | 6.57 | 4 |
| 33 Bis-[(N-allyl)Dmt-NH]hexyl | >10000 | 7.23 | >10000 | 6.83 | 2.5 |

The data presented in Table 4 illustrates the benefit of monoallylation of the inventive Dmt-derivative endomorphin for enhanced μ-opioid antagonism relative to the bioactivity of the comparable diallylation compound.

FIG. 1 illustrates the antagonism of the inventive Dint-Tic analog compounds (9, 10, 11, 18, 19) in the MVD bioassay.

The data presented in FIG. 1 illustrates the enhanced antagonism of the inventive Dmt-Tic analog compounds relative to previously known Dint-Tic compounds, which lack modification of the amino terminus and a spacer.

Figure 2:
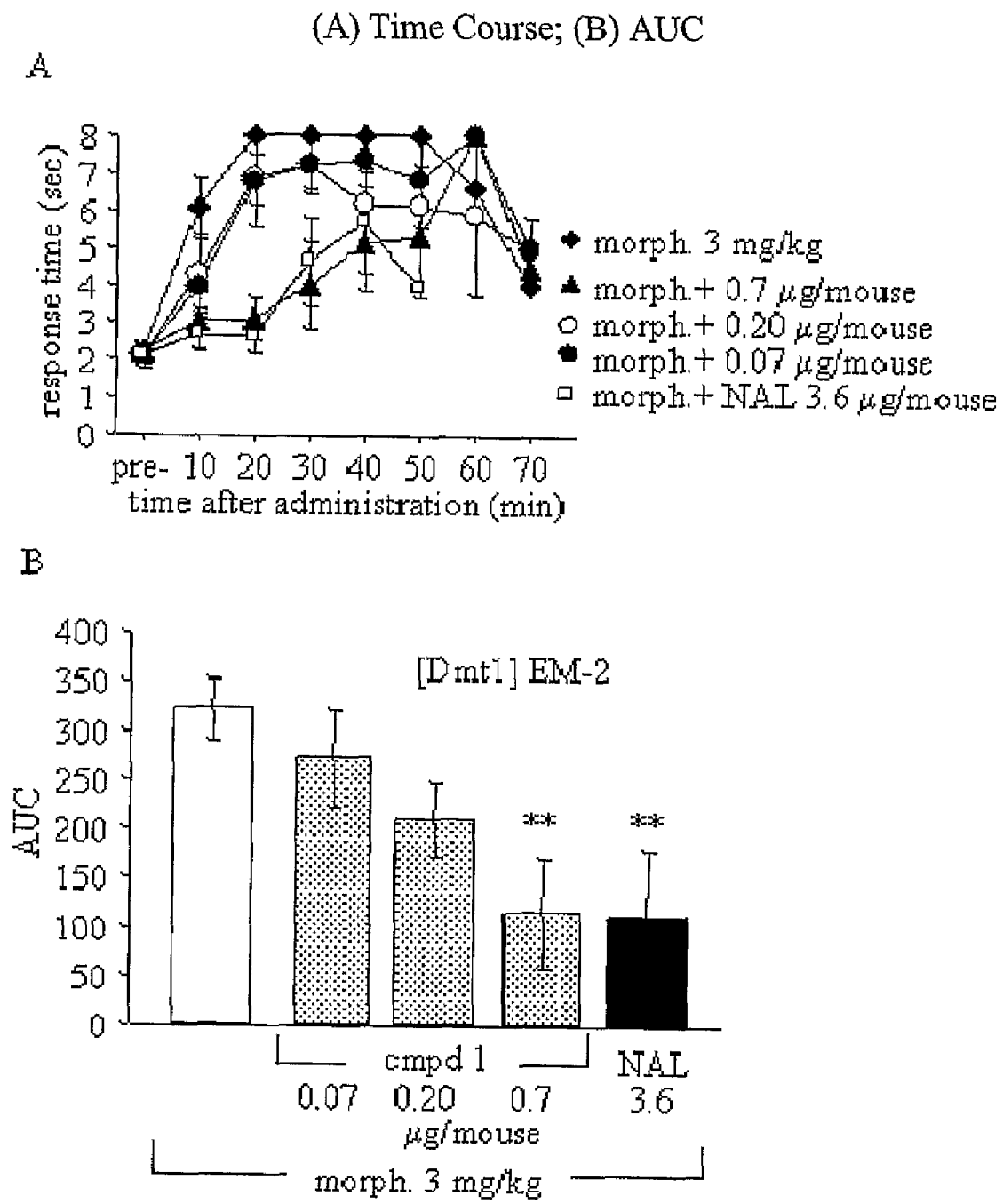
FIG. 2 illustrates in vivo opioid antagonism of compound 31 in a Tail Flick test.

FIG. 2 illustrates in vivo opioid antagonism post administration of compound 31 compound 31 ([N-allyl-Dmt]EM-2) as measured by the tail flick test. Compound 31 antagonizes the effect of opioid bioactivity versus time.

Figure 3:
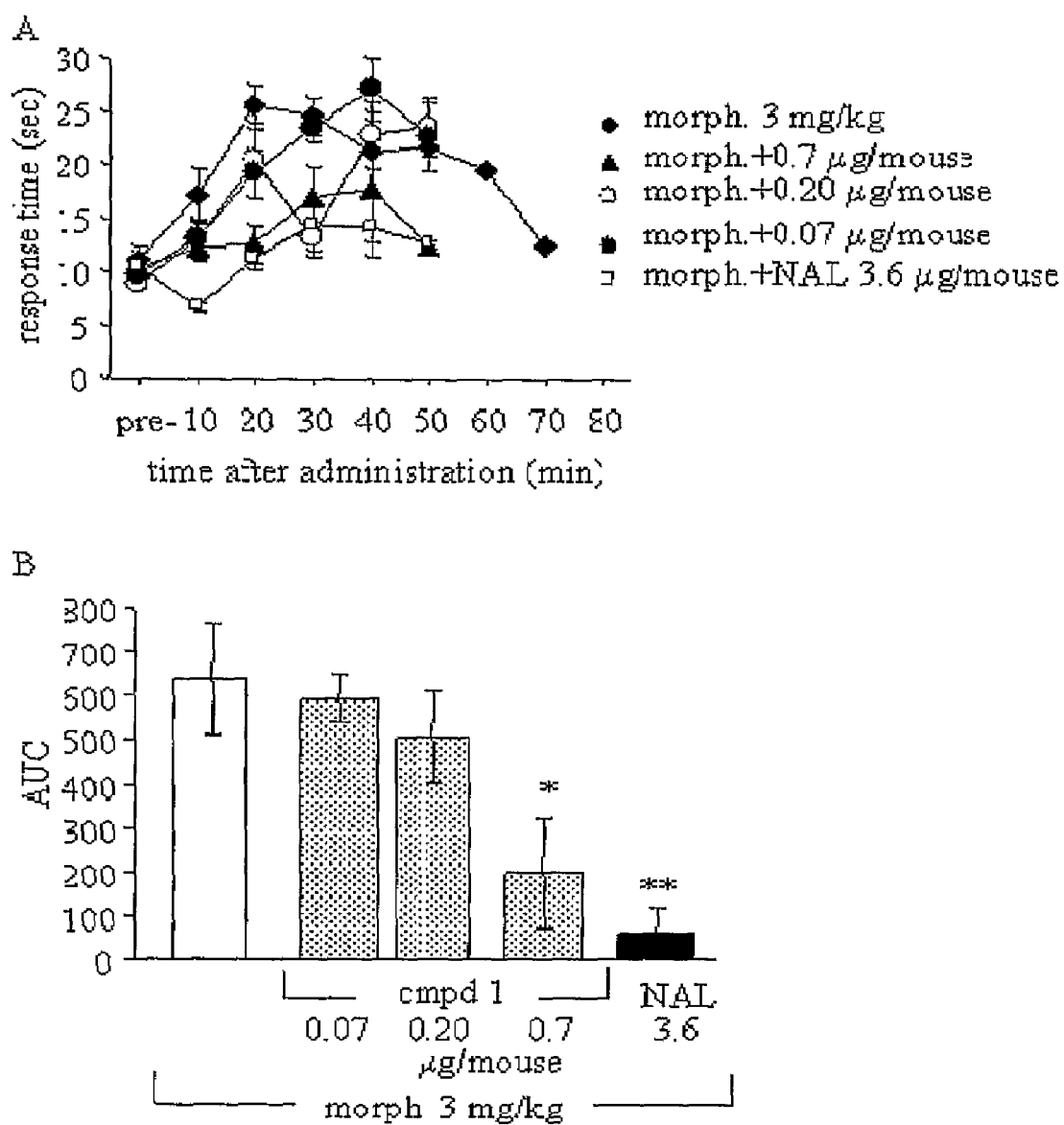
FIG. 3. illustrates in vivo opioid antagonism of compound 31 on morphine analgesia in an HP test.

FIG. 3 illustrates in vivo opioid antagonism of morphine analgesia post administration of compound 31 ([N-allyl-Dmt]EM-2) (31) as measured in an HP test. Compound 31 antagonizes the effect of opioid bioactivity versus time.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of the formula I:

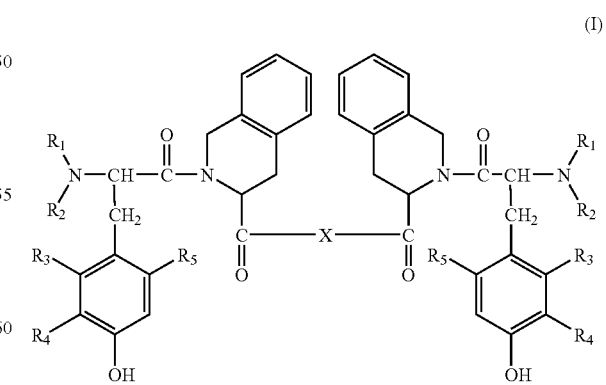

(I)

wherein $R_1$ and $R_2$ are the same or different and each of $R_1$ and $R_2$ is H or $CH_3$;

$R_3$ and $R_5$ are the same or different and each of $R_3$ and $R_5$ is H, $CH_3$, or $C_2H_5$;

$R_4$ is H or $CH_3$;

X is a spacer selected from a group comprising NH—$(CH_2)_n$—NH, wherein n is from 1 to about 20, and 3—NH—$(CH_2)_n$-6—NH—$(CH_2)_m$-2(1H)-pyrazinone, wherein n and m are the same or different and each of n and m is from 1 to about 20.

2. The compound of claim 1, wherein X is NH—$(CH_2)_n$—NH, and wherein n is from 1 to about 10.

3. The compound of claim 1, wherein X is 3—NH—$(CH_2)$n-6—NH—$(CH_2)_m$-2(1H)-pyrazinone, and wherein n and m are the same or different and each of n and m is from 1 to about 20.

4. The compound of claim 3, wherein n is 1 and m is 1.
5. The compound of claim 3, wherein n is 2 and m is 2.
6. The compound of claim 3, wherein n is 3 and m is 3.
7. The compound of claim 3, wherein n is 4 and m is 4.
8. The compound of claim 3, wherein n is 4 and m is 3.
9. The compound of claim 3, wherein n is 3 and m is 4.
10. The compound of claim 3, wherein n is 4 and m is 2.
11. A compound of formula II:

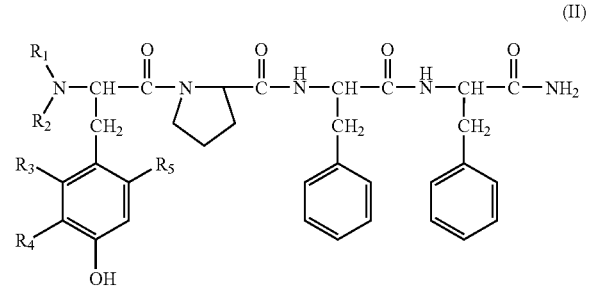

wherein $R_1$ is H or an allyl group;

$R_2$ is an allyl group;

$R_3$ and $R_5$ are the same or different and each of $R_3$ and $R_5$ is H, $CH_3$, or $C_2H_5$; and $R_4$ is H or $CH_3$.

12. The compound of claim 11 wherein $R_1$ is an allyl group; and each of $R_3$ and $R_5$ is $CH_3$.

13. A compound of formula III:

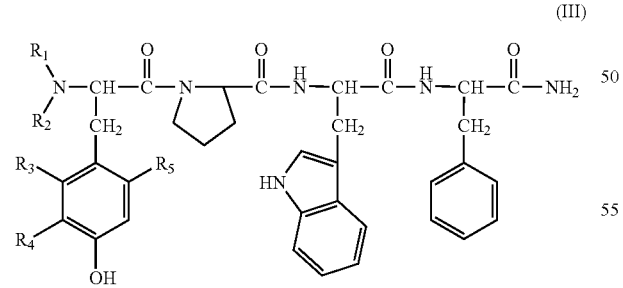

wherein $R_1$ is H or an allyl group;

$R_2$ is an allyl group;

$R_3$ and $R_5$ are the same or different and each of $R_3$ and $R_5$ is H, $CH_3$, or $C_2H_5$; and $R_4$ is H or $CH_3$.

14. The compound of claim 13 wherein $R_1$ is an allyl group; and each of $R_3$ and $R_5$ is $CH_3$.

15. A compound of formula IV:

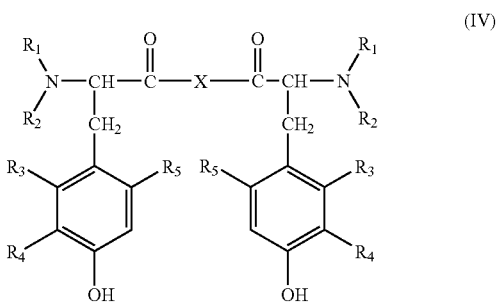

wherein $R_1$ is H or an allyl group;

$R_2$ is an allyl group;

$R_3$ and $R_5$ are the same or different and each of $R_3$ and $R_5$ is H, $CH_3$, or $C_2H_5$;

$R_4$ is H or $CH_3$;

X is a spacer selected from a group comprising NH—$(CH_2)_n$—NH, wherein n is from 1 to about 20, and 3—NH—$(CH_2)$n-6-NH—$(CH_2)$m-2(1H)-pyrazinone, wherein n and m are the same or different and each of n and m is from 1 to about 20.

16. The compound of claim 15, wherein X is NH—$(CH_2)$n—NH, and wherein n is from 1 to about 10.

17. The compound of claim 15, wherein X is 3-NH—$(CH_2)$n-6-NH—$(CH_2)$m-2(1H)-pyrazinone, and wherein n and m are the same or different and each of n and m is from 1 to about 20.

18. The compound of claim 17, wherein n is 1 and m is 1.
19. The compound of claim 17, wherein n is 2 and m is 2.
20. The compound of claim 17, wherein n is 3 and m is 3.
21. The compound of claim 17, wherein n is 4 and m is 4.
22. The compound of claim 17, wherein n is 4 and m is 3.
23. The compound of claim 17, wherein n is 3 and m is 4.
24. The compound of claim 17, wherein n is 4 and m is 2.
25. A compound of formula V:

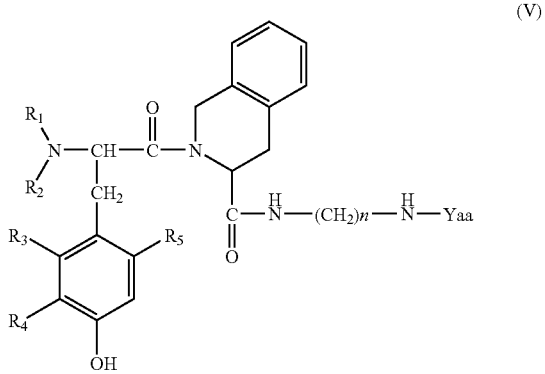

wherein $R_1$ and $R_2$ are the same or different and each of $R_1$ and $R_2$ is H or $CH_3$;

$R_3$ and $R_5$ are the same or different and each of $R_3$ and $R_5$ is H, $CH_3$, or $C_2H_5$;

$R_4$ is H or $CH_3$;

n is from 1 to about 20; and

Yaa is Dmt, Tic, Phe, or another amino acid.

26. A pharmaceutical composition comprising at least one compound of claim 1 and a pharmaceutically acceptable carrier.

27. A pharmaceutical composition comprising at least one compound of claim 11 and a pharmaceutically acceptable carrier.

28. A pharmaceutical composition comprising at least one compound of claim 13 and a pharmaceutically acceptable carrier.

29. A pharmaceutical composition comprising at least one compound of claim 15 and a pharmaceutically acceptable carrier.

30. A pharmaceutical composition comprising at least one compound of claim 25 and a pharmaceutically acceptable carrier.

31. A method of treating a mammal in need of an antagonist of a δ-opioid receptor and an antagonist of a μ-opioid receptor, which method comprises administering at least one compound of claim 1 in an amount that antagonizes a δ-opioid receptor and antagonizes a g-opioid receptor in the mammal.

32. A method of treating a mammal in need of an antagonist of a δ-opioid receptor and an antagonist of a μ-opioid receptor, which method comprises administering at least one compound of claim 11 in an amount that antagonizes a δ-opioid receptor and antagonizes a μ-opioid receptor in the mammal.

33. A method of treating a mammal in need of an antagonist of a δ-opioid receptor and an atagonist of a μ-opioid receptor, which method comprises administering at least one compound of claim 13 in an amount that antagonizes a δ-opioid receptor and antagonizes a μ-opioid receptor in the mammal.

34. A method of treating a mammal in need of an antagonist of a δ-opioid receptor and an atagonist of a μ-opioid receptor, which method comprises administering at least one compound of claim 25 in an amount that antagonizes a δ-opioid receptor and atagonizes a μ-opioid receptor in the mammal.

* * * * *